United States Patent
Nagano et al.

(10) Patent No.: US 7,524,974 B2
(45) Date of Patent: Apr. 28, 2009

(54) FLUORESCENT PROBE

(75) Inventors: Tetsuo Nagano, 1-28-15, Amanuma, Suginami-ku, Tokyo (JP) 167-0032; Yasuteru Urano, Kanagawa (JP); Suguru Kenmoku, Tokyo (JP); Kohjiro Kanda, Saitama (JP)

(73) Assignees: Tetsuo Nagano, Tokyo (JP); Daiichi Pure Chemicals Co., Ltd., Tokyo (JP)

( * ) Notice: Subject to any disclaimer, the term of this patent is extended or adjusted under 35 U.S.C. 154(b) by 450 days.

(21) Appl. No.: 10/519,682

(22) PCT Filed: Jul. 7, 2003

(86) PCT No.: PCT/JP03/08585

§ 371 (c)(1), (2), (4) Date: Aug. 15, 2005

(87) PCT Pub. No.: WO2004/005917

PCT Pub. Date: Jan. 15, 2004

(65) Prior Publication Data

US 2006/0030054 A1 Feb. 9, 2006

(30) Foreign Application Priority Data

Jul. 8, 2002 (JP) ............................ 2002-198197
Jan. 29, 2003 (JP) ............................ 2003-20295

(51) Int. Cl.
C07D 311/90 (2006.01)
(52) U.S. Cl. ................................... 549/224
(58) Field of Classification Search ................ 549/224
See application file for complete search history.

(56) References Cited

U.S. PATENT DOCUMENTS

| | | | |
|---|---|---|---|
| 4,891,075 A | 1/1990 | Dakubu et al. |
| 4,968,631 A | 11/1990 | Dakubu |
| 5,037,615 A | 8/1991 | Kane |
| 5,049,673 A | 9/1991 | Tsien et al. |
| 5,208,148 A | 5/1993 | Haugland et al. |
| 5,246,867 A | 9/1993 | Lakowiez et al. |
| 5,302,731 A | 4/1994 | Pitner et al. |
| 5,340,716 A | 8/1994 | Uiiman et al. |
| 5,380,880 A | 1/1995 | Pitner et al. |
| 5,393,514 A | 2/1995 | Pitner et al. |
| 5,622,821 A | 4/1997 | Selvin et al. |
| 5,623,080 A | 4/1997 | Neckers et al. |
| 5,639,615 A | 6/1997 | Selvin et al. |
| 5,648,270 A | 7/1997 | Kuhn et al. |
| 5,656,433 A | 8/1997 | Selvin et al. |
| 5,800,996 A | 9/1998 | Lee et al. |
| 5,863,727 A | 1/1999 | Lee et al. |
| 5,874,590 A | 2/1999 | Nagano et al. |
| 6,013,802 A | 1/2000 | Hoyland et al. |
| 6,201,134 B1 | 3/2001 | Nagano et al. |
| 6,403,625 B1 | 6/2002 | Nagao et al. |
| 6,441,197 B1 | 8/2002 | Nagano et al. |
| 6,469,051 B2 | 10/2002 | Nagano et al. |
| 6,525,088 B1 | 2/2003 | Nagano et al. |
| 6,569,892 B2 | 5/2003 | Nagano et al. |
| 6,656,927 B1 | 12/2003 | Nagano et al. |
| 6,753,156 B1 | 6/2004 | Mathis et al. |
| 6,756,231 B1 | 6/2004 | Nagano et al. |
| 6,833,386 B2 | 12/2004 | Nagano et al. |
| 6,903,226 B2 | 6/2005 | Nagano et al. |
| 6,936,687 B1 | 8/2005 | Komoriya et al. |
| 6,972,182 B1 | 12/2005 | Colyer et al. |
| 2002/0177120 A1 | 11/2002 | Elliott et al. |
| 2003/0153027 A1 | 8/2003 | Nagano et al. |
| 2003/0157727 A1 | 8/2003 | Nagano et al. |
| 2003/0162298 A1 | 8/2003 | Nagano et al. |

(Continued)

FOREIGN PATENT DOCUMENTS

EP 0314480 5/1989

(Continued)

OTHER PUBLICATIONS

English Language Abstract of JP 2000-239272.

(Continued)

Primary Examiner—Taofiq A Solola
(74) Attorney, Agent, or Firm—Greenblum & Bernstein, P.L.C.

(57) ABSTRACT

A fluorescent probe which is represented by the following formula (I):

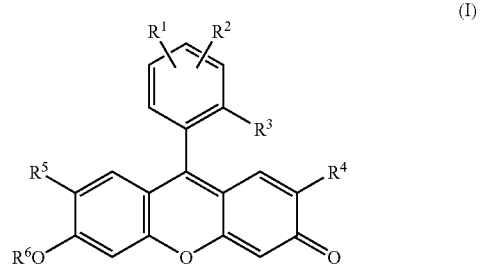

(wherein, $R^1$ and $R^2$ represent hydrogen atom, or a substituent for trapping proton, a metal ion, or an active oxygen species, or the like; $R^3$ represents a monovalent substituent; $R^4$ and $R^5$ represent hydrogen atom or a halogen atom; $R^6$ represents hydrogen atom, an alkylcarbonyl group, or an alkylcarbonyloxymethyl group, provided that a combination of $R^1$, $R^2$, and $R^3$ provides (1) substantially high electron density of the benzene ring to which said groups bind, so that the compound represented by the formula (I) is substantially no fluorescent before the trapping of proton, or the like, and (2) substantially reduced electron density of the benzene ring to which said groups bind, so that a compound after the trapping, which is derived from the compound represented by the formula (I) is substantially highly fluorescent after the trapping of proton or the like). A fluorescent probe having an excellent fluorescence property is provided.

17 Claims, 6 Drawing Sheets

U.S. PATENT DOCUMENTS

| | | | |
|---|---|---|---|
| 2004/0043498 | A1 | 3/2004 | Nagano et al. |
| 2004/0147035 | A1 | 7/2004 | Nagano et al. |
| 2005/0037332 | A1 | 2/2005 | Komatsu et al. |
| 2005/0064308 | A1 | 3/2005 | Nagano et al. |
| 2005/0123478 | A1 | 6/2005 | Nagano et al. |
| 2005/0130314 | A1 | 6/2005 | Nagano et al. |
| 2005/0182253 | A1 | 8/2005 | Yano et al. |
| 2006/0030054 | A1 | 2/2006 | Nagano et al. |

FOREIGN PATENT DOCUMENTS

| | | |
|---|---|---|
| EP | 0515133 | 11/1992 |
| EP | 0582836 | 2/1994 |
| EP | 1069121 | 1/2001 |
| EP | 1260508 | 11/2002 |
| EP | 1260510 | 11/2002 |
| JP | 60-054381 | 3/1985 |
| JP | 6-207112 | 7/1994 |
| JP | 6-211831 | 8/1994 |
| JP | 8-271430 | 10/1996 |
| JP | 9-101262 | 4/1997 |
| JP | 10-088124 | 4/1998 |
| JP | 10-226688 | 8/1998 |
| JP | 5-180773 | 7/1999 |
| JP | 2000-111480 | 4/2000 |
| JP | 2000-239272 | 5/2000 |
| JP | 2000-239272 | 9/2000 |
| WO | 89/09408 | 10/1989 |
| WO | 96/42016 | 12/1996 |
| WO | 98/15830 | 4/1998 |
| WO | 99/15896 | 4/1999 |
| WO | 99/51586 | 10/1999 |
| WO | 00/00819 | 1/2000 |
| WO | 01/62755 | 8/2001 |
| WO | 01/63265 | 8/2001 |
| WO | 01/64664 | 9/2001 |
| WO | 2004/040296 | 5/2004 |
| WO | 2005/024049 | 3/2005 |
| WO | 2005/085811 | 9/2005 |

OTHER PUBLICATIONS

English Language Abstract of JP 9-101262.
English Language Abstract of JP 5-180773.
English Language Abstract of JP 10-88124.
English Language Abstract of JP 2000-111480.
English Language Abstract of JP 60-054381.
English Language Abstract of JP 6-211831.
Rajendra Nath Sen et al., "The Condensation of Primary Alcohols with Resorcinol and Other Hydroxy Aromatic Compounds", J. Am. Chem. Soc., vol. 47, pp. 1079-1091 (1925), XP002332482.
R. Kurduker et al., "Search for Physiologically Active Compounds", Proc. Indian. Acad. Sci. Sect. A., vol. 57, pp. 280-287 (1963).
A. Minta et al., "Fluorescent Indicators for Cytosolic Calcium Based on Rhodamine and Fluorescein Chromophores", J. Biol. Chem., vol. 264, No. 14, pp. 8171-8178 (1989).
P.K. Grover et al., "Xanthones. Part IV. A New Synthesis of Hydroxyxanthones and Hydroxybenzophenones," J. Chem. Sci. (London), pp. 3982-3985 (1955).
Reyes, J.G., et al., Biol. Res., 27, pp. 49-56, 1994.
Tsuda, M., et al., Neurosci., 17, pp. 6678-6684, 1997.
Koike, T., et al., J. Am. Chem. Soc., 118, pp. 12696-12703, 1996.
Saibou Kougaku (Cell Technology), 17, pp. 584-595, 1998.
Tanpakushitsu.Kakusan.Kouso (Protein, Nucleic Acid and Enzyme), extra No. 42, pp. 171-176, 1997.
Tetsuji Kametani, Nankodo Co., Ltd., pp. 214-215, 1997.
Handbook of Fluroescent Probes and Research Chemicals, 6th Edition by Richard P. Haugland, pp. 503 and 531-540.
Protective Groups in Organic Synthesis, T. W. Greene, John Wiley & Sons, Inc. pp. v-xxi and 369-405.
Angew. Chem., Int. Ed. (1999), 38(21), pp. 3209-3212.
Anal. Chem. (1998), 70(13), pp. 2446-2453.
Bioorganic & Medicinal Chemistry, vol. 4, No. 6, pp. 901-916, (1996).
Bioorg. Khim. (1995), 21(10), pp. 795-801.
Sci. China, Ser. B: Chem. (1998), 41(5), pp. 549-555.
J. Am. Chem. Soc. (1996), 118, pp. 6514-6515.
Hirano T. et al., "Highly Zinc-Selective Fluorescent Sensor Molecules Suitable for Biological Applications", J. Am. Chem. Soc., vol. 122, No. 49, Dec. 13, 2000, pp. 12399-12400.
Walkup G. K. et al., "A New Cell-Permeable Fluorescent Probe for $Zn^{2+}$", J. Am. Chem. Soc., vol. 122, No. 23, Jun. 14, 2000, pp. 5644-5645.
Bambot, S.B. et al., "Potential Applications of Lifetime-Based, Phase-Modulation Fluorimetry in Bioprocess and Clinical Monitoring", Trends in Biotechnology, vol. 13, No. 3, Mar. 1995, pp. 106-115, XP 004207135.
Sipior, J. et al., "Lifetime-Based Optical Sensing of pH Using Resonance Energy Transfer in Sol-Gel Films", Sensors and Actuators B; vol. 22, No. 3, Dec. 1994, pp. 181-188, XP004011062.
Selvin, P.R. et al., "Luminescence Energy Transfer Using a Terbium Chelate: Improvements on Fluorescence Energy Transfer", Proceedings of the National Academy of Science of USA, National Academy of Science, Washington, DC, US, vol. 91, Oct. 1994, pp. 10024-10028.
Yuan, J. et al., "Functionalization of Fluorescent Lanthanide Complexes and Their Applications to Biotechnology", Bunseki Kagaku—Japan Analyst; vol. 48, No. 12, pp. 1077-1083 (1999), XP002932633.
Rogers, M. V., Drug Discovery Today, vol. 2, pp. 156-160, 1997.
Selvin, P. R., et al., J. Am. Chem. Soc., vol. 117, pp. 8132-8138, 1995.
Stryer, L., Ann. Rev. Biochem., vol. 47, pp. 819-846, 1978.
Hemmilä, I., et al., Drug Discovery Today, vol. 2, pp. 373-381, 1997.
New Apoptosis Experimental Protocol, 2nd ed., Yodosha, pp. 201-204, 1999.
Selvin, P. R., et al., J. Am. Chem. Soc., vol. 116, pp. 6029-6030, 1994.
J. Burch, "The Inhibition of Horse-Liver Esterase by Rhodamine B," Biochemical Journal, vol. 59, pp. 97-110 (1955).
D.D. Thomas et al., "Fluorescence energy transfer in the rapid-diffusion limit," Proceedings of the National Academy of Sciences of the United States of America, vol. 75, No. 12, pp. 5746-5750 (1978).
S.M. Yeh et al., "Characterization of Transferin Metal-Binding Sites by Diffusion-Enhanced Energy Transfer," Biochemistry, 19, pp. 5057-5062 (1980).
R.A. Edwards et al., "Spectroscopic Studies of Cibacron Blue and Congo Red Bound to Dehydrogenases and Kinases. Evaluation of Dyes and Probes of the Dinucleotide Fold," Biochemistry, vol. 18, No. 23, pp. 5197-5204 (1979).
C.F. Meares et al., "Diffusion-Enhanced Energy Transfer Shows Accessibility of Ribonucleic Acid Polymerase Inhibitor Binding Sites," Biochemistry, 20, pp. 610-617 (1981).
T.G. Wensel et al., "Electrostatic Properties of Myoglobin Probed by Diffusion-Enhanced Energy Transfer," Biochemistry, 22, pp. 6247-6254 (1983).
M.M. Federici et al., "Interaction of Cibacron Blue $F_3GA$ with Slutamine Synthetase: Use of the Dye as a Conformational Probe. 1. Studies Using Unfractionated Dye Samples," Biochemistry, 24, pp. 647-660 (1985).
T.G. Wensel et al., "Diffusion-Enhanced Lanthanide Energy-Transfer Study of DNA-Bound Cobalt(III) Bleomycins: Comparisons of Accessibility and Electrostatic Potential with DNA Complexes of Ethidium and Acridine Orange," Biochemistry, 24, pp. 3060-3069 (1985).
B.S. Isaacs et al., "A Domain of Membrane-Bound Coagulation Factor Va Is Located Far from the Phospholipid Surface. A Fluorescence Energy Transfer Measurement," Biochemistry, 25, pp. 4958-5969 (1986).
T.G. Wensel et al., "Study of Biological Macromolecules by Diffusion-Enhanced Lanthanide Energy Transfer," Journal of the Less-Common Metals, 149, pp. 143-160 (1989).
P.R. Selvin et al., "Luminescent Resonance Energy Transfer," Journal of the American Chemical Society, 116, pp. 6029-6030 (1994).
T. Yamamoto et al., "Determination of Electrostatic Potential Around Specific Locations on the Surface of Actin by Diffusion-enhanced Fluorescence Resonance Energy Transfer," Journal of Molecular Biology, 241, pp. 714-731 (1994).

S.C.J. Meskers et al., "Analysis of Delayed Luminescence from Some Quenchers of $Tb(DPA)_3^{3-}$ Emission: Proof for an Energy Transfer Quenching Mechanism," Journal of Alloys and Compounds, 250, pp. 332-335 (1997).

D.D. Root, "In situ Molecular Association of Dystrophin with Actin Revealed by Sensitized Emission Immuno-Resonance Energy Transfer," Proceedings of the National Academy of Sciences of the United States of America, 94, pp. 5685-5690 (1997).

C. Mucignat-Caretta et al., "Building of Two Fluorescent cAMP Analogues to Type I and II Regulatory Subunits of cAMP-Dependent Protein Kinases," Biochimica et Biophysica Acta, 1357, pp. 81-90 (1997).

Y.-W. Park et al., "Homogeneous Proximity Tyrosine Kinase Assays: Scintillation Proximity Assay versus Homogeneous Time-resolved Fluorescence," Analytical Biochemistry, 269, pp. 94-104 (1999).

K. Blomberg et al., "Terbium and Rhodamine as Labels in a Homogeneous Time-resolved Fluorometric Energy Transfer Assay of the β Subunit of Human Chorionic Gonadotropin in Serum," Clinical Chemistry, 45, 855-861 (1999).

L.L. Pearce et al., "Role of Metallothionein in Nitric Oxide Signaling as Revealed by a Green Fluorescent Fusion Protein," Proceedings of the National Academy of Scienecs of the United States of America, 97, pp. 477-482 (2000).

M. Koresawa et al., "Development of a Time-Resolved Fluorometric Detection System Using Diffusion-Enhanced Energy Transfer," Analytical Chemistry, 72, p. 4904-4907 (2000).

T. Nagano et al., "Specific Detection Method and Useful Generating System of Singlet Oxygen," Free Radicals in Clinical Medicine, vol. 7, pp. 35-41 (1993).

I. Saito et al., "Methyl-Substituted Poly(vinylnaphthalene) as a Reversible Singlet Oxygen Carrier," J. Am. Chem. Soc., vol. 107, pp. 6329-6334, 1985.

T. W. Greene et al., "Protective Groups in Organic Synthesis," John Wiley & Sons, Inc., pp. v-xxi and 369-405 (1981).

J. Kabatc et al., "Free Radical Polymerization Initiated via Photoinduced Intermolecular Electron Transfer Process: Kinetic Study $3^1$," Polymer 40(3), pp. 735-745 (1999).

K. Setsukinai et al., "Fluorescence Switching by O-dearylation of 7-aryloxycoumarins. Development of Novel Fluorescence Probes to Detect Reactive Oxygen," J. Chem. Soc., Perkin Trans. 2, 12, pp. 2453-2457, (2000).

J.W. Firth et al., "Some Phenoxy-2H-benzo[b]pyrans," J. Chem. Research (S), vol. 2000, No. 7, pp. 308-308 (Jul. 2000).

J.G. Reyes et al., "A Fluorescence Method to Determine Picomole Amounts of Zn(II) in Biological Systems," Biol. Res., vol. 27, pp. 49-56, (1994).

M. Tsuda et al., "Expression of Zinc Transporter Gene, ZnT-1, Is Induced After Transient Forebrain Ischemia in the Gerbil," The Journal of Neuroscience, vol. 17, No. 17, pp. 6678-6684 (Sep. 1, 1997).

T. Koike et al., "A Novel Biomimetic Zinc(II)—Fluorophore, Dansylamidoethyl-Pendant Macrocyclic Tetraamine 1,4,7,10-Tetraazacyclododecane (Cyclen)," J. Am. Chem. Soc., vol. 118, 1996, pp. 12696-12703.

Web site of the Pharmaceutical Society of Japan, on Feb. 1, 2003, a copy of the screenshot is enclosed. The subject matter of the screenshot was then published in an Abstract of "The 123rd Annual Congress of the Pharmaceutical Society of Japan" on Mar. 5, 2003 for presentation No. 29[P1]I-219 entitled "Development of Fluorescent Probe Having Low Affinity for Zinc" in the 123rd Annual Congress of the Pharmaceutical Society of Japan held on Mar. 27-29, 2003.

Newport Green: A Catalog of Molecular Probes, Inc. "Handbook of Fluorescent Probes and Research Chemical, Chapter 22—Section 22.7 Fluorescent Indicators for $Zn^{2+}$ and Other Metals", 6th Edition by Richard P. Haugland, pp. 531-510 (1996).

Toshiaki Hiratsuka, "Tanpakushitsu-Kakusan-Kouso (Protein, Nucleic Acid and Enzyme)", vol. 42, No. 7, pp. 171-176 (1997).

Anderegg et al., Helvetica Chimica Acta, Vo. 50, pp. 2330-2333 (1967).

T. Hirano et al., "Highly Zinc-Selective Flouorescent Sensor Molecules Suitable for Biological Applications," Journal of the American Chemical Society, vol. 122, No. 49, pp. 12399-12400 (2000).

R.P. Haugland, "Handbook of Fluorescent probes and Research Products," 9th Edition Supplement, Chapter 20, pp. 805-817 (2002).

G.K. Walkup et al., "A New Cell-Permeable Fluorescent Probe for $Zn^{2+}$," Journal of the American Chemical Society, vol. 122, No. 23, pp. 5644-5645 (2000).

J. Kawakami et al., "*Ab initio* Molecular Orbital Study of Emission Mechanism of 2,6-Bis (quinolinecarboxy) methylpyridine as Fluorescent Chemosensors for Zinc and Cadmium Ions," Journal of Computer Chemistry, Japan, vol. 2, No. 2, pp. 57-62 (2003).

C.J. Frederickson et al., "A quinoline fluorescence method for visualizing and assaying the histochemically reactive zinc (bouton zinc) in the brain," Journal of Neuroscience Methods, vol. 20, pp. 91-103 (1987).

D. Zalewski et al., "Correlation of apoptosis with change in intracellular labine Zn(II) using Zinquin [(2-methyl-8-*p*-toluenesulphonamido-6-quinolyloxy)acetic acid], a new specific fluorescent probe for Zn(II)," Biochemical Journal, vol. 296, Part 2, pp. 403-408 (1993).

William A. Pryor et al., "A Practical Method for Preparing Peroxynitrite Solutions of Low Ionic Strength and Free of Hydrogen Peroxide," Free Radical Biology & Medicine, vol. 18, No. 1, pp. 75-83 (1995).

Stephen L. Hempel et al., "Dihydrofluorescein Diacetate is Superior for Detecting Intracellular Oxidants: Comparison with 2',7'-Dichlorodihydrofluorescein Diacetate, 5(and 6)-Carboxy-2',7'-Dichlorodihydrofluorescein Diacetate, and Dihydrorhodamie 123," Free Radical Biology & Medicine, vol. 27, Nos. 1/2, pp. 146-159 (1999).

Joseph A. Hrabie et al., "New Nitric Oxide-Releasing Zwitterions Derived from Polyamines," J. Org. Chem. vol. 58, pp. 1472-1476 (1993).

English Language Abstract of JP 10-226688, published Aug. 25, 1998.

English Language Abstract of JP 2000-239272, published Sep. 5, 2000.

English Language Abstract of JP 6-207112, published Jul. 26, 1994.

English Language Abstract of JP 8-271430, published Oct. 18, 1996.

L. Lindqvist et al., "Radiationless Transitions in Xanthene Dyes", J. Chem. Phys., vol. 44, pp. 1711-1712 (1966).

Richard P. Haugland, Handbook of Fluorescent Probes and Research Chemicals, Sixth Edition, Chapters 22-24, pp. 503-584 (1996).

Theodora W. Greene, Protective Groups in Organic Synthesis, Chapter 7, pp. 218-287 (1981).

U.S. Appl. No. 10/598,371 to Nagano et al.

Conceptual diagram of PET

Fluorescein

FLUORESCENT PROBE

TECHNICAL FIELD

The present invention relates to a fluorescent probe. More specifically, the present invention relates to a fluorescent probe which traps proton, a metal ion, or active oxygen species and emits fluorescence.

BACKGROUND ART

Fluorescein, a fluorescent substance known from the 19th century, can be excited at around 500 nm in an aqueous solution, and has a high quantum yield. For this reason, the substance has been commonly used as a fundamental scaffold of fluorescent probes. For example, fluorescein is used as a fundamental nucleus of a fluorescent probe for nitrogen monoxide (Japanese Patent Laid-Open No. 10-226688(1998)), a fluorescent probe for zinc (WO 01/62755), or the like.

6-Hydroxy-9-phenylfluorone, in which the carboxyl group of fluorescein is substituted with hydrogen atom, has a lower fluorescence quantum yield. Accordingly, the carboxyl group is believed to have a role in characteristics as a fluorophore of fluorescein (Lindqvist, L., et al., J. Chem. Phys., 44, 1711-12, 1966). From the above reason, the carboxyl group is preserved in fluorescein derivatives proposed so far to avoid deterioration of the fluorescent property of fluorescein. Therefore, almost no compound is known wherein the carboxyl group is converted to other functional group.

DISCLOSURE OF THE INVENTION

An object of the present invention is to provide a fluorescent probe with an excellent fluorescence property. The inventors of the present invention conducted various researches on characteristics of fluorescein as an fluorescent substance, and during the course of the researches, they have come to a conclusion that the fluorescence properties of fluorescein essentially derive from the tricyclic xanthene skeleton, and the 2-carboxyphenyl group binding to the 9-position of the xanthene ring has absolutely no substantial effect on the fluorescence properties. The inventors of the present invention evaluated fluorescence properties of compounds wherein the carboxyl group of the 2-carboxyphenyl group is substituted with a substituent other than hydrogen atom, such as methyl group or methoxy group. Surprisingly, they found that the compounds had intensities of fluorescence quantum yield almost equal to that of fluorescein, and the compounds had almost the same excitation wavelength and fluorescence wavelength as those of fluorescein.

On the basis of the above findings and the fact that 6-hydroxy-9-phenylfluorone, in which the carboxyl group of fluorescein is replaced with hydrogen atom, gave a lowered fluorescence quantum yield, the inventors of the present invention concluded that a role of the carboxyl group of fluorescein is to prevent a free rotation due to the carbon-carbon single bond between the xanthene ring and the benzene ring, thereby a pathway of deactivation of a fluorophore in an excitation state without a luminescence process can be prevented. Further, the inventors of the present invention conducted researches to develop a fluorescent probe having a high fluorescence property based on the above findings. As a result, they found that a compound, wherein the phenyl group which binds to the 9-position of the xanthene ring has sufficiently high electron density, is substantially non-fluorescent, whilst a compound wherein said phenyl group has sufficiently low electron density is highly fluorescent, and that a fluorescent probe having a desired fluorescence property can be logically designed by adjusting the electron density of said phenyl group with conversion of the carboxyl group of fluorescein to other functional group. The present invention was achieved on the basis of the above findings.

The present invention thus provides a fluorescent probe which is represented by the following formula (I):

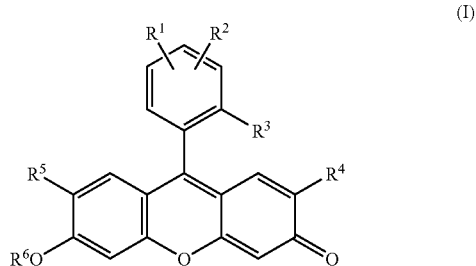

(wherein, $R^1$ and $R^2$ each independently represents hydrogen atom, or a substituent for trapping proton, a metal ion, or an active oxygen species, provided that both of $R^1$ and $R^2$ do not simultaneously represent hydrogen atoms, or $R^1$ and $R^2$ may combine to each other to form a ring structure for trapping proton, a metal ion, or active oxygen species; $R^3$ represents a monovalent substituent other than hydrogen atom, carboxyl group, or sulfonic acid group; $R^4$ and $R^5$ each independently represents hydrogen atom or a halogen atom; $R^6$ represents hydrogen atom, an alkylcarbonyl group, or an alkylcarbonyloxymethyl group, provided that a combination of $R^1$, $R^2$, and $R^3$ provides:

(1) substantially high electron density of the benzene ring to which said groups bind so that the compound represented by the formula (I) is substantially no fluorescent before the trapping of proton, a metal ion, or an active oxygen species, and (2) substantially reduced electron density of the benzene ring to which said groups bind so that a compound after the trapping, which is derived from the compound represented by the formula (I), is substantially highly fluorescent after the trapping of proton, a metal ion, or an active oxygen species).

According to preferred embodiments of the present invention, provided are the aforementioned fluorescent probe, wherein the oxidation potential of said benzene ring before the trapping of proton, a metal ion, or an active oxygen species is less than 1.40 V, and oxidation potential of said benzene ring after trapping of proton, a metal ion, or an active oxygen species is 1.40 V or higher, and said oxidation potential of said benzene ring increases by 0.20 V or higher after the trapping, under a sufficiently basic condition so that the hydroxy group of the xanthene ring can become a complete anion when $R^6$ is hydrogen atom; the aforementioned fluorescent probe, wherein the oxidation potential of said benzene ring before the trapping of proton, a metal ion, or an active oxygen species is less than 1.70 V, and the oxidation potential of said benzene ring after the trapping of proton, a metal ion, or an active oxygen species is 1.70 V or higher, and the oxidation potential of said benzene ring increases by 0.20 V or higher after the trapping, under a sufficiently acidic condition so that the hydroxy group of the xanthene ring can exist in a non-dissociation state when $R^6$ is hydrogen atom; the aforementioned fluorescent probe wherein $R^3$ is a lower alkyl group or a lower alkoxy group; the aforementioned fluorescent probe wherein the metal ion is an alkali metal ion, calcium ion, magnesium ion, or zinc ion; and the aforementioned fluorescent probe wherein the active oxygen species is selected from the group consisting of nitrogen monoxide, hydroxy radical, singlet oxygen, and superoxide.

According to more preferred embodiments of the present invention, provided are the aforementioned fluorescent probe which is for measuring zinc ion or nitrogen monoxide and wherein either or both of $R^1$ and $R^2$ are a group represented by the following formula (A):

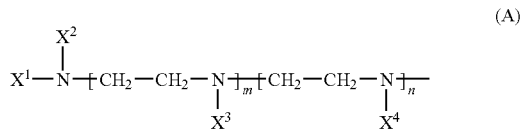

(A)

(wherein $X^1$, $X^2$, $X^3$, and $X^4$ each independently represents hydrogen atom, an alkyl group, 2-pyridylmethyl group, or a protective group of amino group, and m and n each independently represents 0 or 1); and the aforementioned fluorescent probe which is for measuring singlet oxygen and wherein $R^1$ and $R^2$ combine to each other to represent a ring structure represented by the following formula (B):

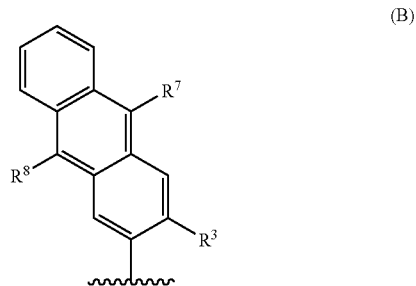

(B)

(wherein $R^7$ and $R^8$ each independently represents a $C_{1-4}$ alkyl group or an aryl group).

From another aspect, provided by the present invention is a method for designing a fluorescent probe which is represented by the aforementioned general formula (I) (wherein, $R^1$ and $R^2$ each independently represents hydrogen atom, or a substituent for trapping proton, a metal ion, or an active oxygen species, provided that both of $R^1$ and $R^2$ do not simultaneously represent hydrogen atoms, or $R^1$ and $R^2$ may combine to each other to form a ring structure for trapping proton, a metal ion, or an active oxygen species; $R^3$ represents a monovalent substituent other than hydrogen atom, carboxyl group, or sulfonic acid group; $R^4$ and $R^5$ each independently represents hydrogen atom or a halogen atom; $R^6$ represents hydrogen atom, an alkylcarbonyl group, or an alkylcarbonyloxymethyl group), which comprises a step of selecting, as a combination of $R^1$, $R^2$, and $R^3$, the combination which provides:

(1) substantially high electron density of the benzene ring to which said groups bind so that the compound represented by the formula (I) is substantially no fluorescent before the trapping of proton, a metal ion, or an active oxygen species, and (2) substantial reduced electron density of the benzene ring to which said groups bind so that a compound after the trapping, which is derived from the compound represented by the formula (I), is substantially highly fluorescent after the trapping of proton, a metal ion, or an active oxygen species. Further, a fluorescent probe obtained by the aforementioned design method is also provided by the present invention.

BEST MODE FOR CARRYING OUT THE INVENTION

Figure 1:
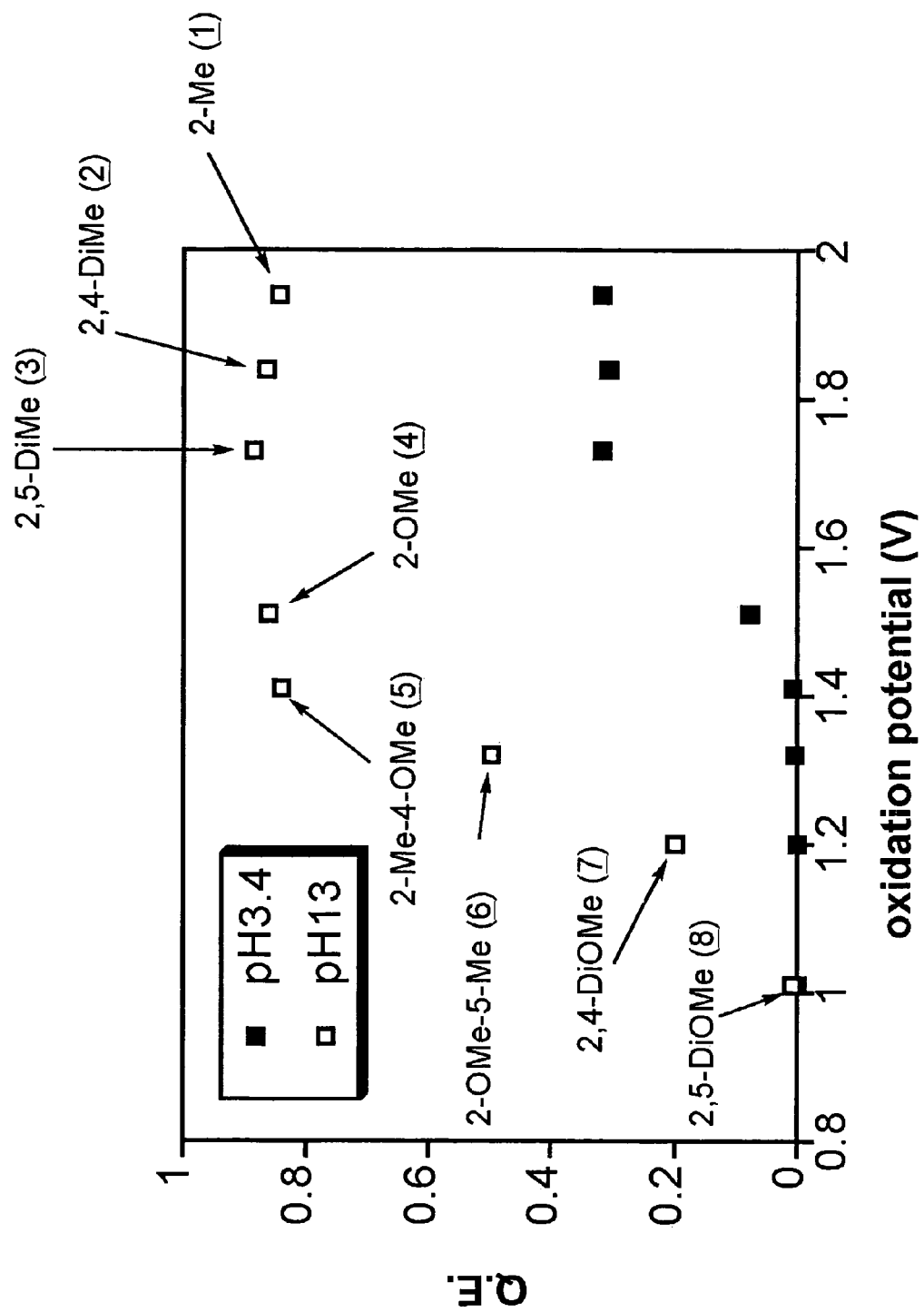
FIG. 1 shows, as for derivatives wherein the carboxyl group of fluorescein is converted to an alkyl group or an alkoxy group (Compounds 1 to 8), a correlation between fluorescence quantum yield of each compound and oxidation potential of the benzene ring moiety as a PET donor.

The fluorescent probe provided by the present invention which is represented by the formula (I) is used as a fluorescent probe for measuring proton, a metal ion, or an active oxygen species (which is sometimes referred to as "a measuring object" in the specification,). As the metal ion, examples include alkali metal ions such as sodium ion and lithium ion, alkaline earth metal ions such as calcium ion, magnesium ion, and zinc ion. As the active oxygen species, examples include nitrogen monoxide, hydroxy radical, singlet oxygen, and superoxide. However, measuring objects are not limited to these examples.

The fluorescent probe of the present invention is characterized in that the carboxyl group of the 2-carboxyphenyl group binding at the 9-position of the xanthene ring of various fluorescent probes for measuring variety of measuring objects, which have been proposed so far on the basis of the fundamental skeleton of fluorescein, is converted to a monovalent substituent other than hydrogen atom or sulfonic acid group (in the formula (I), said substituent is represented by $R^3$). On the benzene ring which binds to the 9-position of the xanthene ring, two substituents are present either of which or a combination of which participates in trapping of a measuring object (in the formula (I), these substituents are represented by $R^1$ and $R^2$, either of which may sometimes represent hydrogen atom).

As $R^1$ and $R^2$ in the compound represented by the formula (I), substituents for trapping a measuring object, which have been used so far for fluorescent probes for measuring proton, a metal ion, or an active oxygen species, can be used. $R^1$ and $R^2$ on the benzene ring may combine to each other to form a ring structure and thereby forms a substituent for trapping proton, a metal ion, or an active oxygen species. For example, as a combination of $R^1$ and $R^2$ on the benzene ring, groups shown below can be used. However, the combinations are not limited to these examples (2-substituted phenyl groups which bind to the 9-position of the xanthene ring or rings condensed with said phenyl group are shown).

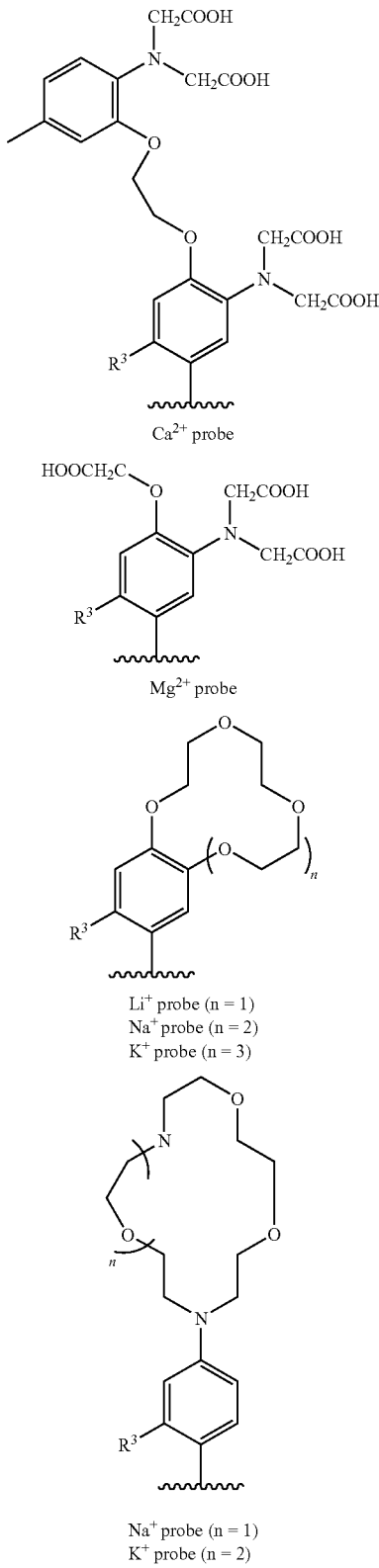

Ca²⁺ probe

Mg²⁺ probe

Li⁺ probe (n = 1)
Na⁺ probe (n = 2)
K⁺ probe (n = 3)

Na⁺ probe (n = 1)
K⁺ probe (n = 2)

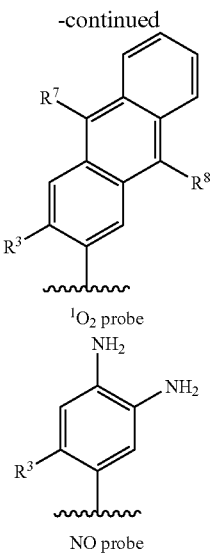

¹O₂ probe

NO probe

The substituting positions of $R^1$ and $R^2$ on the benzene ring are not particularly limited. On the benzene ring to which $R^1$, $R^2$, and $R^3$ bind, any substituent other than these substituents may be present. Various kinds of substituents for trapping a measuring object have been proposed, and accordingly, a person skilled in the art can suitably select a substituent depending on the type of a measuring object. For example, Japanese Patent Laid-Open No. 10-226688, WO 99/51586, Japanese Patent Laid-Open No. 2000-239272, and WO 01/62755 can be referred to. Substituents for trapping measuring objects can also be used which are described in Chapter 22 (calcium ion, magnesium ion, zinc ion, and the other metal ions), Chapter 23 (pH indicator), and Chapter 24 (sodium ion, potassium ion, chloride ion, and the other inorganic ions) of a catalog of Molecular Probes Inc. (Handbook of Fluorescent Probes and Research Chemicals, Sixth edition). However, substituents for trapping measuring objects are not limited to those described in the aforementioned publications.

In the specification, the term "trapping" should be construed in its broadest sense which includes trapping of a metal ion, such as chelating which causes substantially no chemical transformation of $R^1$ and/or $R^2$, as well as trapping causing a change of the chemical structures of $R^1$ and/or $R^2$ by chemical reaction with a measuring object, and should not be construed in any limitative sense.

For example, for a fluorescent probe for measuring zinc ion or nitrogen monoxide, either or both of $R^1$ and $R^2$ are preferred to be a group represented by the following formula (A):

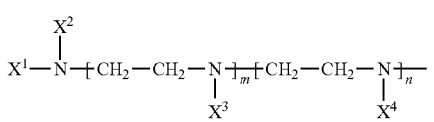
(A)

(wherein $X^1$, $X^2$, $X^3$, and $X^4$ each independently represents hydrogen atom, an alkyl group, 2-pyridylmethyl group, or a protective group of amino group, and m and n each independently represents 0 or 1).

For a fluorescent probe for measuring singlet oxygen, both of $R^1$ and $R^2$ independently represent a group represented by the aforementioned formula (A) wherein m and n represent 0, and $R^1$ and $R^2$ substitute on the benzene ring in adjacent positions to each other. For a fluorescent probe for measuring zinc ion, preferably, either of $R^1$ and $R^2$ is a group represented by the aforementioned formula (A) and the other is hydrogen atom, wherein $X^1$, $X^2$, $X^3$, and $X^4$ are preferably 2-pyridylmethyl groups, and more preferably $X^1$ and $X^2$ are 2-pyridylmethyl groups. Symbol m is preferred to be 0, n is preferred to be 1, and $X^4$ is preferred to be hydrogen atom, wherein both of $X^1$ and $X^2$ are preferred to be 2-pyridylmethyl groups.

For a fluorescent probe for measuring singlet oxygen, $R^1$ and $R^2$ preferably combine to each other to represent a ring structure represented by the following formula (B):

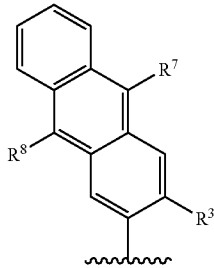

(B)

(wherein $R^7$ and $R^8$ each independently represents a $C_{1-4}$ alkyl group or an aryl group). $R^7$ and $R^8$ each independently is preferably a phenyl group which may be substituted, and more preferably both of $R^7$ and $R^8$ are phenyl group. The aforementioned formula (B) represents a group which binds in the 9-position of the xanthene ring, and one or more substituents may be present at any substitutable positions on the ring of the aforementioned formula (B).

In the specification, "an alkyl group" or an alkyl moiety of a substituent containing the alkyl moiety (for example, an alkylcarbonyl group or an alkylcarbonyloxymethyl group) means, for example, a linear, branched, or cyclic alkyl group, or an alkyl group comprising a combination thereof having 1 to 12 carbon atoms, preferably 1 to 6 carbon atoms, and more preferably 1 to 4 carbon atoms. More specifically, a lower alkyl group (an alkyl group having 1 to 6 carbon atoms) is preferred as the alkyl group. Examples of the lower alkyl group include methyl group, ethyl group, n-propyl group, isopropyl group, cyclopropyl group, n-butyl group, sec-butyl group, isobutyl group, tert-butyl group, cyclopropylmethyl group, n-pentyl group, and n-hexyl group. When the term "a halogen atom" is referred to in the specification, a halogen may be any one of fluorine atom, chlorine atom, bromine atom, or iodine atom, and preferably, fluorine atom, chlorine atom, or bromine atom.

As $R^3$, a lower alkyl group or a lower alkoxy group is preferred. Particularly preferred is methyl group or methoxy group. As the halogen atom represented by $R^4$ and $R^5$, chlorine atom or fluorine atom is preferred. $R^4$ and $R^5$ each independently is preferably hydrogen atom, chlorine atom, or fluorine atom. As the alkylcarbonyl group represented by $R^6$, for example, acetyl group or the like can be used. As the alkylcarbonyloxymethyl group represented by $R^6$, acetoxymethyl group or the like can be used. $R^6$ is preferred to be hydrogen atom, acetyl group, or acetoxymethyl group. In a group represented by the formula (A), types of the protective group of amino group are not particularly limited. For example, p-nitrobenzene sulfonyl group, trifluoroacetyl group, trialkylsilyl group, or the like can be used appropriately. As for the protective groups of amino group, for example, "Protective Groups in Organic Synthesis," (T. W. Greene, John Wiley & Sons, Inc. (1981)) can be referred to.

In the fluorescent probe of the present invention, a combination of $R^1$, $R^2$, and $R^3$ is selected as a combination which provides (1) substantially high electron density of the benzene ring to which $R^1$, $R^2$, and $R^3$ bind so that the compound represented by the formula (I) is substantially no fluorescent before trapping of a measuring object, and (2) substantially reduced electron density of the benzene ring to which $R^1$, $R^2$, and $R^3$ bind so that a compound after trapping of a measuring object, derived from the compound represented by the formula (I), is substantially highly fluorescent.

Information of the electron density of the benzene ring to which $R^1$, $R^2$, and $R^3$ bind is easily available, for example, by calculating oxidation potential of said benzene ring according to a quantum chemical means. A reduction of the oxidation potential of said benzene ring means an increase of the electron density of said benzene ring, which corresponds to an elevation of HOMO orbital energy. For example, HOMO energy of said benzene ring moiety can be determined by a density functional theory (B3LYP/6-31G(d)). As $R^1$ and $R^2$, substituents should be selected which change the oxidation potential after trapping of a measuring object. All the oxidation potentials described in the specification are indicated as values obtained by using Ag/Ag+ as a reference electrode.

The hydroxy group on xanthene ring becomes an anion after dissociation of its proton in an alkaline solution at pH 13. For example, under such condition, a compound wherein oxidation potential of said benzene ring is 1.00 V or lower may sometimes be substantially no fluorescent, whilst when the oxidation potential of said benzene ring is 1.40 V or higher, the compound may sometimes be substantially strongly fluorescent, as specifically shown in Examples in the specification. Further, under an acidic condition at pH 3.4, for example, a compound wherein the oxidation potential of said benzene ring is 1.40 V or lower may substantially be no fluorescent, whilst when the oxidation potential of said benzene ring is 1.70 V or higher, the compound may sometimes be substantially strongly fluorescent. When the combination of $R^1$, $R^2$, and $R^3$ is selected by using the oxidation potential of said benzene ring as a criterion, a fluorescent probe having an excellent fluorescent property can be obtained by selecting a combination which provides (1) substantially high electron density of said benzene ring in a compound before trapping of a measuring object, and (2) substantially reduced electron density of said benzene ring after trapping of a measuring object.

As the combination of $R^1$, $R^2$, and $R^3$, a combination is preferred such that the oxidation potential of said benzene ring before the trapping of a measuring object is lower than 1.40 V, the oxidation potential of said benzene ring after the trapping of a measuring object is 1.40 V or higher, and the oxidation potential of said benzene ring increases by 0.20 V or higher, preferably 0.30 V or higher, more preferably 0.35 V or higher, and most preferably 0.40 V or higher after the trapping, under a sufficiently basic condition so that the hydroxy group of the xanthene rings exists as a substantially complete anion when $R^6$ is hydrogen atom. As the basic condition, a condition at pH 12 or higher, preferably pH 13 can be applied.

Similarly, when $R^6$ is hydrogen atom, and under a sufficiently acidic condition so that the hydroxy group of the xanthene rings can exist as substantially complete non-dissociation state, a combination is preferred such that the oxidation potential of said benzene ring before the trapping of a measuring object is less than 1.70 V, and the oxidation potential of said benzene ring after the trapping of a measuring object is 1.70 V or higher, and the oxidation potential of said benzene ring increases by 0.20 V or higher, preferably 0.25 V or higher, and most preferably 0.30 V or higher after the trapping of a measuring object. As the acidic condition, a condition at pH 4.0 or less, preferably pH 3.4 can be applied.

Although it is not intended to be bound by any specific theory, the above mentioned findings discovered by the inventors of the present invention can be explained by PET (Photoinduced Electron Transfer). PET is one of methods for fluorescence quenching, wherein electron transfer from neighboring electron donating moiety (PET donor) occurs to induce fluorescence quenching faster than a rate where the singlet-excited fluorophore generated by irradiation of excitation light returns to a ground state with fluorescence emission. When the compound represented by the formula (I) is divided for consideration as a xanthene ring moiety which acts as a fluorophore and a benzene ring moiety which quench the fluorescence (PET donor), if the oxidation potential of the benzene ring is low (i.e., higher electron density and higher HOMO energy), the fluorescence derived from the xanthene ring will be quenched through the PET.

As fluorescent probes, compounds are required to have a feature that the probe is substantially no fluorescent before trapping of a measuring object and changes to substantially strongly fluorescent substance after trapping of a measuring object. Therefore, a probe having a significant change in fluorescence intensity can be chosen as a preferable probe. For example, a probe can be designed so that its fluorescence is quenched through PET before the trapping of a measuring object and substantially no PET is induced after trapping of a measuring object. When a fluorescent probe introduced with a new substituents as $R^1$, $R^2$, and/or $R^3$ is designed by using the oxidation potential of said benzene ring moiety as a criterion, a correlation between the oxidation potential of the benzene ring after the introduction of the functional group and weakening of a fluorescence can sometimes be predicted from the knowledge so far available. Nevertheless, the correlation between the oxidation potential and the fluorescence intensity is preferably determined by the method specifically described in Examples of the specification.

Further, for example, when a fluorescent probe for measuring nitrogen monoxide is designed, an electron density of the adjacent amino groups represented by $R^1$ and $R^2$ (either of said amino groups may be substituted, for example, with an alkyl group) can be increased, thereby reactivity between nitrogen monoxide and the amino groups is increased and sensitivity of the fluorescent probe can be heightened. It was revealed that, in the conventional fluorescent probes on the basis of fluorescein as a fundamental skeleton, the carboxyl group on the benzene ring is electronegative, thereby electron densities of said amino groups are lowered, and as a result, reactivity is reduced. Accordingly, when electron donating groups such as an alkyl group and an alkoxy group are used as $R^3$ in the fluorescent probe of the present invention, electron density of the benzene ring is increased, and as a result, substantial non-fluorescence before trapping of nitrogen monoxide can be maintained, and the electron densities of said amino groups are increased to improve reactivity with nitrogen monoxide. Similarly, in a fluorescent probe for measuring singlet oxygen, by heightening electron density of the reactive group represented by the aforementioned formula (B), reactivity with singlet oxygen can be increased, which enables maintenance of substantial non-fluorescent property of a fluorescent probe before trapping of singlet oxygen.

The term "measurement" used in the present specification should be construed in its broadest sense, including quantification, qualification, measurements performed for the purpose of diagnosis, tests, detections and the like. The method for measuring a measuring object using the fluorescent probe of the present invention generally comprises the steps of (a) reacting a compound represented by the aforementioned formula (I) with a measuring object; and (b) measuring fluorescence of a compound generated in the aforementioned process (a). For example, the fluorescent probe of the present invention or a salt thereof may be dissolved in an aqueous medium such as physiological saline or a buffered solution, or in a mixture of the aqueous medium and a water-miscible solvent such as ethanol, acetone, ethylene glycol, dimethyl sulfoxide, and dimethylformamide, the resultant solution may be added to a suitable buffered solution containing cells or tissues, and then the fluorescence spectra may be measured.

Fluorescence of the compounds after trapping a measuring object can be measured by an ordinary method. For example, a method of measuring fluorescence spectra in vitro, or a method of measuring fluorescence spectra in vivo by a bioimaging technique can be employed. For example, when a quantitative measurement is conducted, a calibration curve is desired to be prepared in advance according to an ordinary method. When a compound wherein $R^6$ in the formula (I) is $C_{1-12}$ alkylcarbonyl group or acetoxymethyl group is used, the compound permeates cell membranes and is taken into cells, generating a product with the alkylcarbonyl group or acetoxymethyl group hydrolyzed by an esterase present in the cytoplasm. The hydrolyzed compound is not easily excreted out of the cell, and react with an intracellular measuring object to give a fluorescent compound. Accordingly, by using these compounds as a measuring agent, a measuring object which localizes in an individual cell can be measured by a bioimaging technique with high sensitivity.

As the fluorescent probe of the present invention, as well as the compound represented by the aforementioned formula (I), a salt thereof may be used. Types of the salt are not particularly limited. Examples of the salt include, for example, mineral acid salts such as hydrochloride, sulfate, and nitrate; and organic acid salts such as methanesulfonate, p-toluenesulfonate, oxalate, citrate, and tartrate as acid addition salts, and metal salts such as sodium salts, potassium salts, calcium salts, and magnesium salts; ammonium salts; and organic amine salts such as triethylamine salts as base addition salts. In addition, salts of amino acids such as glycine may be formed. The fluorescent probe according to the present invention may be used as a composition by mixing with additives generally used for an agent preparation, if necessary. For example, as additives for a use of the agent under a physiological condition, additives such as dissolving aids, pH adjusters, buffers, isotonic agents and the like can be used, and amounts of these additives can suitably be chosen by those skilled in the art. The compositions may be provided as those in appropriate forms, for example, powdery mixtures, lyophilized products, granules, tablets, solutions and the like.

From another aspect, the compound provided by the present invention is represented by the following formula (II)

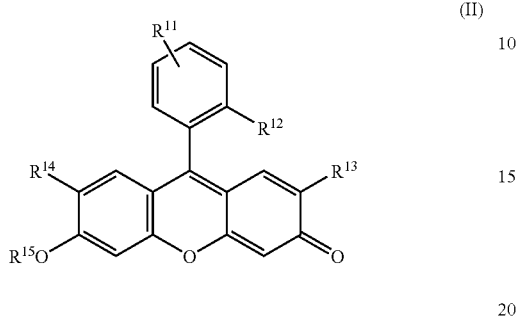
(II)

(wherein $R^{11}$ represents hydrogen atom, an alkyl group, or an alkoxy group; $R^{12}$ represents an alkyl group or an alkoxy group; $R^{13}$ and $R^{14}$ each independently represents hydrogen atom or a halogen atom; and $R^{15}$ represents hydrogen atom, an alkylcarbonyl group, or an alkylcarbonyloxymethyl group). As $R^{11}$, hydrogen atom, a $C_{1-4}$ alkyl group, or a $C_{1-4}$ alkoxy group is preferred, and hydrogen atom, methyl group, or methoxy group is preferred. As $R^{12}$, a $C_{1-4}$ alkyl group, or a $C_{1-4}$ alkoxy group is preferred, methyl group or methoxy group is more preferred. $R^{13}$, $R^{14}$, and $R^{15}$ are preferred to be hydrogen atom. The compound can be used as a pH sensor.

A preferable combination of substituents for the pH sensor is not particularly limited. For example, a compound wherein one of $R^{11}$ and $R^{12}$ is methyl group, and the other is methoxy group, and all of $R^{13}$, $R^{14}$, and $R^{15}$ are hydrogen atoms is non-fluorescent in an acidic range, therefore the change in pH can be precisely measured. When $R^{11}$ is hydrogen atom and $R^{12}$ is methyl group or methoxy group, or when a both of $R^{11}$ and $R^{12}$ are methyl groups, a compound wherein $R^{13}$ and/or $R^{14}$ is fluorine atom or chlorine atom is preferable for measurement of pH change by the ratio method. Further, a compound wherein $R^{15}$ is acetyl group or acetoxymethyl group is preferable for a pH sensor for measuring intracellular pH change.

EXAMPLES

The present invention will be explained more specifically by referring to the following examples. However, the scope of the present invention is not limited to these examples.

Example 1

Preparation of Compounds

The following compounds are prepared. These compounds are designed so that a compound having greater compound number had a lower oxidation potential of the benzene ring binding in the 9-position of the xanthene ring (i.e., so as to have a higher the electron density, in other words, have a higher HOMO orbital energy). Preparation schemes of the compound having unsubstituted benzene ring and Compound 1 are shown below.

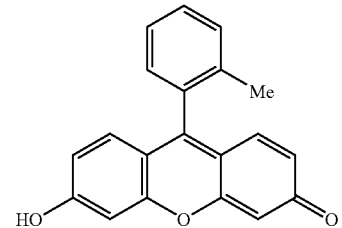
1

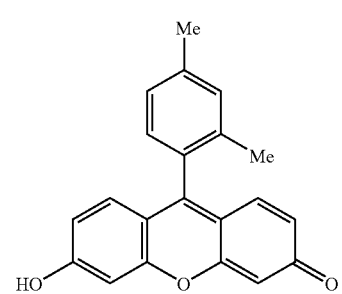
2

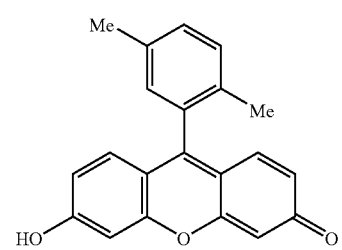
3

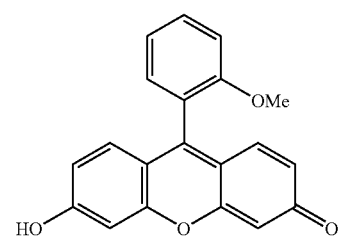
4

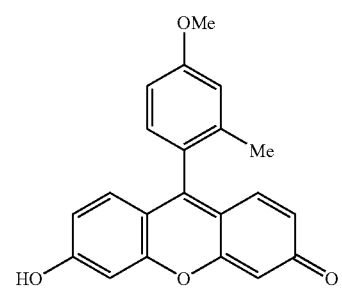
5

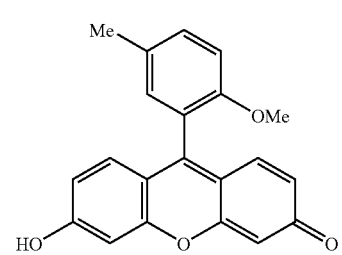
6

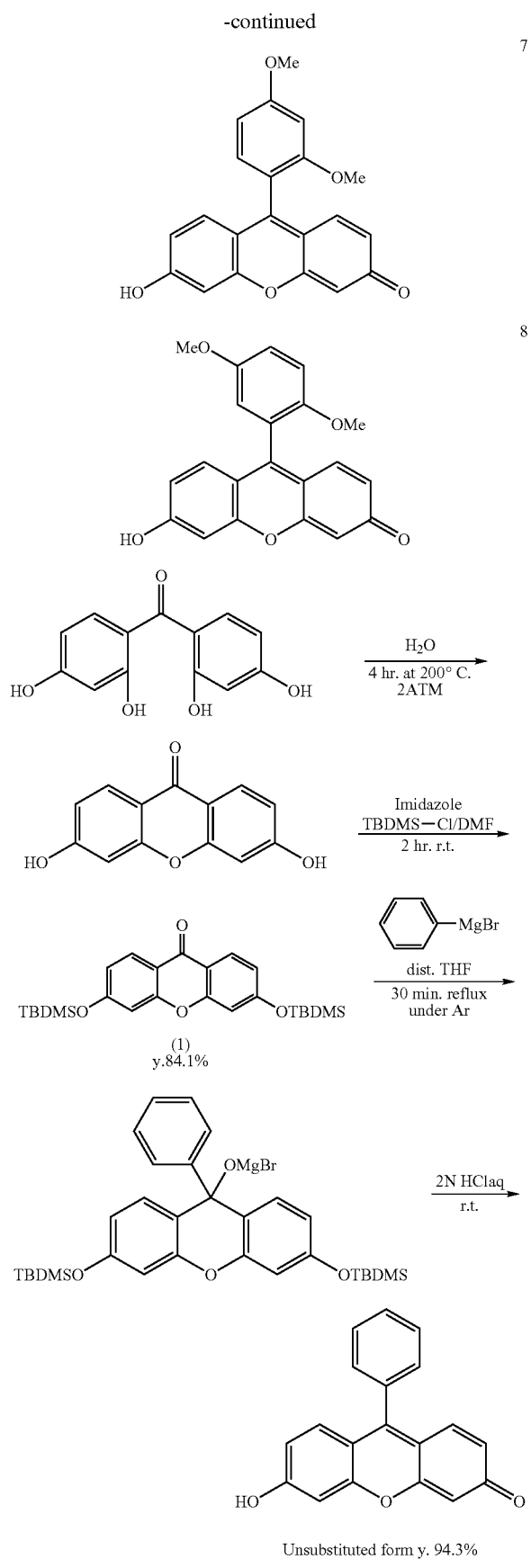

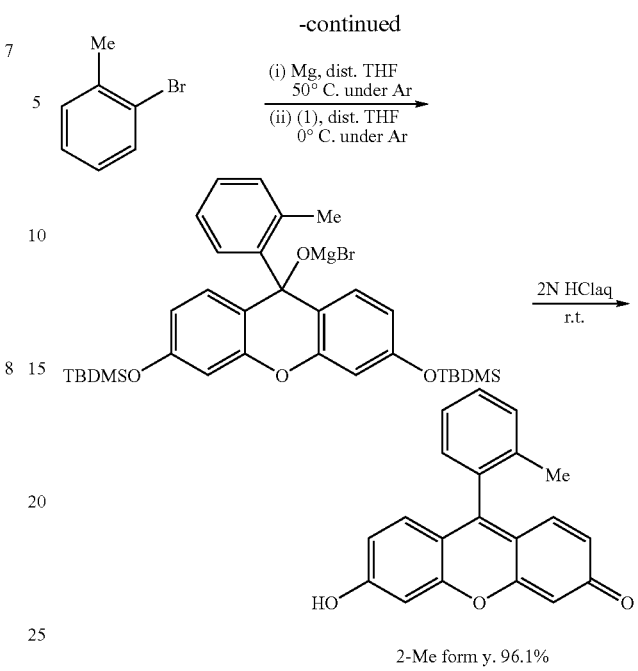

2-Me form y. 96.1%

Xanthone was prepared according to the method described in Proc. Indian. Acad. Sci. Sect. A., 57, 280(1963), and the resulting xanthone was converted to di(tert-butyldimethylsilyl) protected form (xanthone-TBDMS) (J. Biol. Chem., 264, 14, 8171(1989)). Mg (109 mg, 4.50 mmol) was placed in a well dried vessel, and heated under stirring at 250° C. for 180 minutes while being kept under a reduced pressure by using a vacuum pump. After being left for cooling, the vessel was substituted with argon and added with 2-bromotoluene (77 mg, 0.45 mmol) dissolved in distilled THF (2 ml), and then gradually heated up to 60° C. When a change of the reaction solution to dark green was observed, the solution was cooled with ice. The reaction solution was added with xanthone-TBDMS (137 mg, 0.300 mmol) dissolved in distilled THF (2 ml), and stirred for 10 minutes. The reaction solution was added with 2N HCl solution (10 ml) and stirred to deposit yellow solid. The solid was collected by filtration, washed with a small amount of THF, and dried to obtain yellow solid (87 mg, yield 96%).

$^1$H-NMR (300 MHz, DMSO) δ 2.00 (3H, s), 7.01 (2H, d, J=9.15 Hz), 7.10 (2H, s), 7.21 (2H, d, J=9.15 Hz), 7.31 (1H, d, J=7.14 Hz), 7.52 (3H, m) MS(E1) 302 (M+).

Compound 2 to Compound 8 were obtained in a similar manner.

Compound 2

$^1$H-NMR (300 MHz, DMSO) δ 1.97 (3H, s), 2.42 (3H, s), 7.01 (2H, d, J=9.15 Hz), 7.10(2H, s), 7.21 (4H, m), 7.34 (1H, s) MS(E1) 316 (M+).

Compound 3

$^1$H-NMR (300 MHz, DMSO) δ 1.95 (3H, s), 2.35 (3H, s), 6.99 (2H, d, J=9.15 Hz), 7.05(2H, s), 7.12 (1H, s), 7.21 (2H, d, J=9.15 Hz), 7.39 (2H, m) MS(E1) 316 (M+).

Compound 4

$^1$H-NMR (300 MHz, DMSO) δ 3.70(3H, s), 7.02 (2H, d, J=9.20 Hz), 7.08 (2H, s), 7.23(2H, t, J=7.50 Hz), 7.34 (4H, m), 7.68 (1H, m) MS(E1) 318 (M+).

Compound 5

$^1$H-NMR (300 MHz, DMSO) δ 1.98 (3H, s), 3.86 (3H, s), 6.96 (2H, d, J=9.15 Hz), 7.03 (3H, m), 7.10 (1H, s), 7.23 (1H, d, J=8.22 Hz), 7.28 (2H, d, J=9.15 Hz) MS(E1) 332 (M+).

Compound 6

$^1$H-NMR (300 MHz, DMSO) δ 2.33 (3H, s), 3.66 (3H, s), 7.07 (2H, d, J=9.15 Hz), 7.14 (3H, m), 7.26 (1H, d, J=8.88 Hz), 7.42 (1H, d, J=9.15 Hz), 7.48 (1H, d, J=8.88 Hz) MS(E1) 332 (M+).

Compound 7

$^1$H-NMR (300 MHz, DMSO) δ 3.70 (3H, s), 3.91 (3H, s), 6.83 (1H, d, J=8.43 Hz), 6.89 (1H, s), 7.06 (2H, d, J=9.36 Hz), 7.12 (2H, s), 7.26 (1H, d, J=8.43 Hz), 7.47 (2H, d, J=9.36 Hz) MS(E1) 348 (M+).

Compound 8

$^1$H-NMR (300 MHz, DMSO) δ 3.64(3H, s), 3.76 (3H, s), 6.96 (1H, s), 7.04 (2H, d, J=9.15 Hz), 7.10 (2H, s), 7.23 (1H, d, J=9.15 Hz), 7.30 (1H, d, J=9.15 Hz), 7.23 (2H, d, J=9.15 Hz) MS(E1) 348 (M+).

Example 2

A correlation between a fluorescence quantum yield and the oxidation potential of the benzene ring moiety of each of the above prepared compounds was studied. The results are shown in FIG. 1. As clearly shown by the results in the figure, the fluorescence quantum yield of each compound changed depending on the oxidation potential of the benzene ring moiety. In an alkaline solution at pH13, the OH group of the xanthene ring dissociates its proton to become an anion, and under this condition, the compound became almost non-fluorescent at an oxidation potential of 1.00 V or lower, whereas at an oxidation potential of 1.40 V or higher, the compound emitted fluorescence with a quantum yield of almost 1. Between the two values, a decrease in the quantum yield was observed with a decrease in the oxidation potential. Under an acidic condition at pH 3.4, an oxidation potential of the benzene ring, at which a change in fluorescence was observed, was changed as compared to that under a basic condition, i.e., the compound was almost no fluorescent at an oxidation potential of 1.40 V or lower, whereas at an oxidation potential of 1.70 V or higher, the compound emitted fluorescence with a quantum yield of almost 0.3. It is known that the OH group of the xanthene ring is protonated at pH 3.4, and under this condition, the quantum yield of Fluorescein is about 0.3.

Example 3

Figure 2:
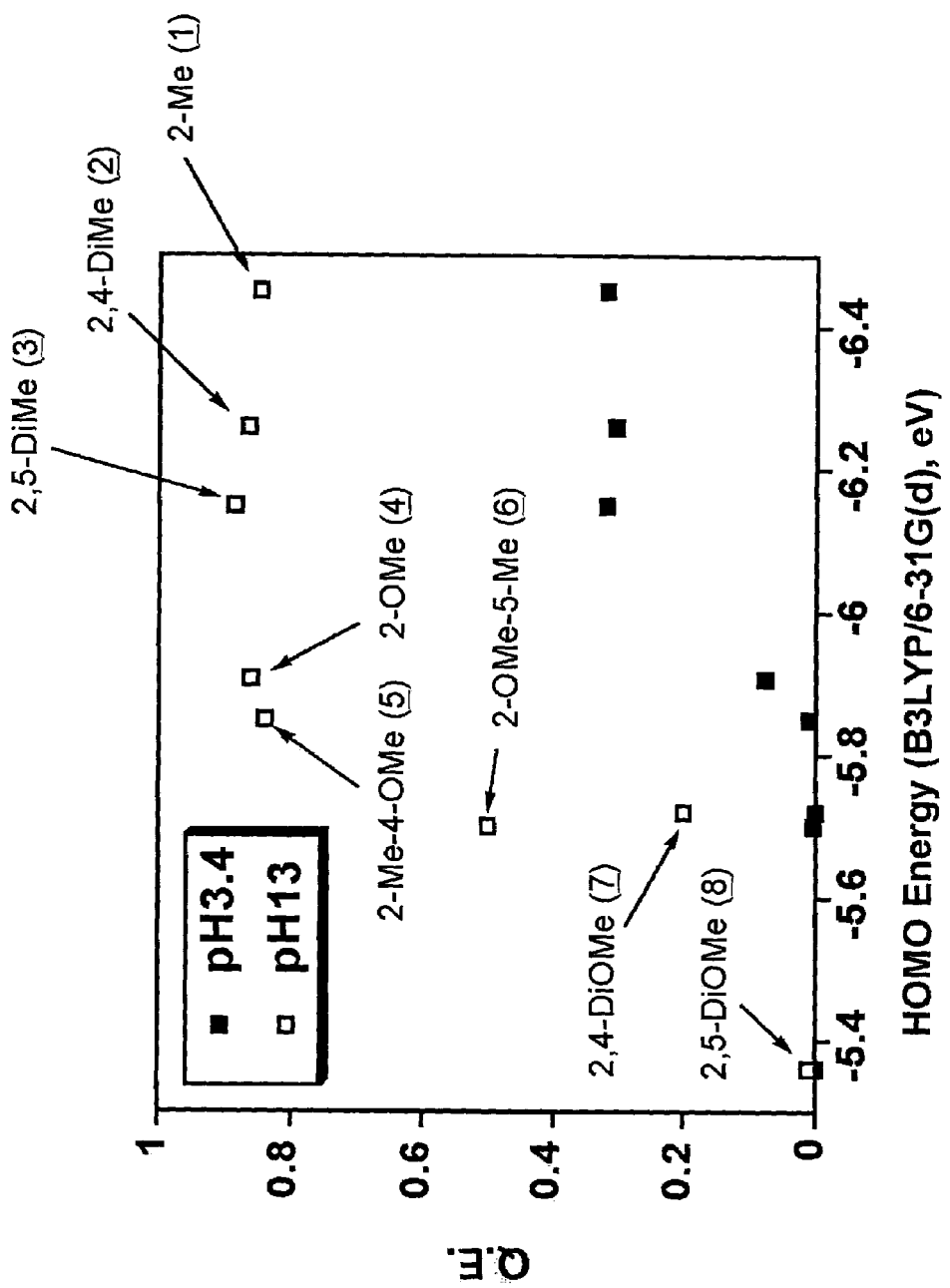
FIG. 2 shows, as for derivatives wherein the carboxyl group of fluorescein is converted to an alkyl group or an alkoxy group (Compounds 1 to 8), a correlation between the fluorescence quantum yield of each compound and HOMO energy level of the benzene ring moiety as a PET donor.

Oxidation potential of a compound is generally predictable by a quantum chemistry calculation. HOMO energies of the benzene ring moiety of the aforementioned compounds were determined by the density functional theory (B3LYP/6-31G (d)), and correlation between the determined values and the fluorescence quantum yield was plotted. As a result, almost the same result was obtained as that of Example 2 wherein oxidation potential was used as a criterion (FIG. 2). From the result, the fluorescence property of the compound of the present invention was proved to be quantitatively predictable by a quantum chemical calculation. On the basis of these findings, a logical designing method of a fluorescent probe of the present invention can be conducted.

Example 4

Figure 3:
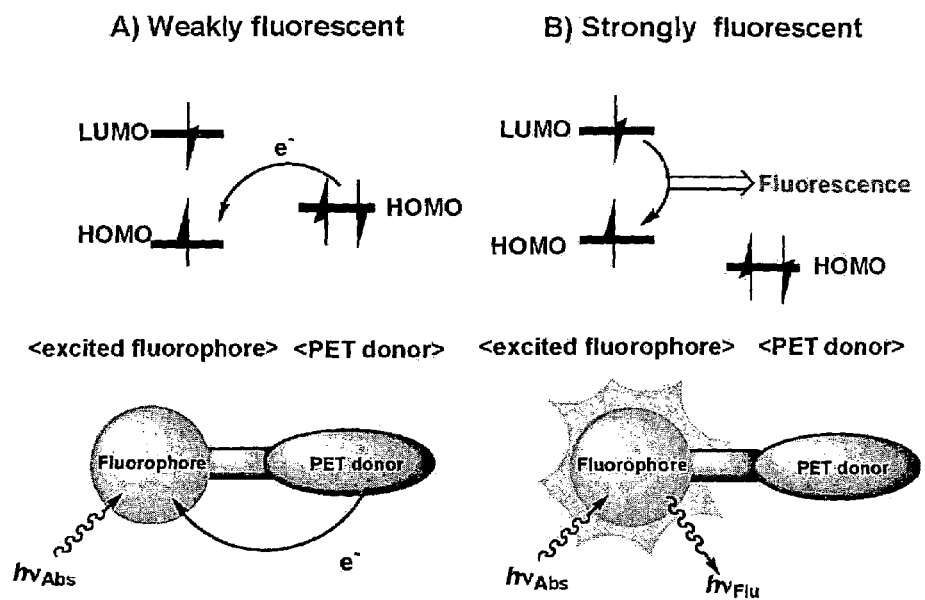
FIG. 3 shows a conceptual diagram of PET and two moieties (i.e, PET donor moiety and a fluorophore) of fluorescein.
Figure 3:
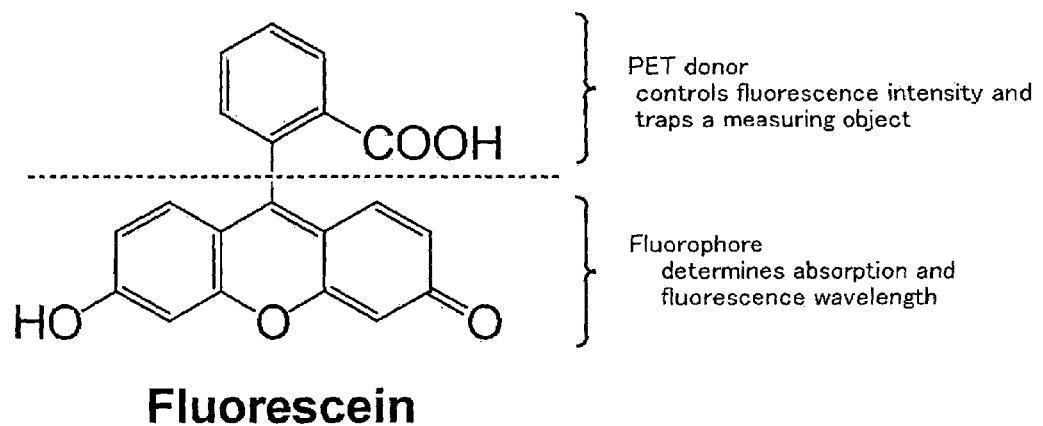

PET (Photoinduced Electron Transfer) is one of methods for fluorescence quenching, wherein electron transfer from neighboring electron donating moiety (PET donor) occurs to induce fluorescence quenching faster than a rate where the singlet-excited fluorophore generated by irradiation of excitation light returns to a ground state with fluorescence emission. When the compound of the present invention is divided into a xanthene ring moiety which is a fluorophore and a benzene ring moiety which quench the fluorescence (PET donor) for consideration, if the oxidation potential of the benzene ring is low (i.e., higher electron density, in other words, higher HOMO energy), the fluorescence derived from xanthene is quenched through PET. In fact, the two moieties have revealed to be almost orthogonal to each other from an X-ray crystal structure analysis, and Compounds 1 to 8 have almost the same excitation and fluorescence wavelengths. Accordingly, the hypothesis wherein the compound of the present invention is divided into the two moieties for consideration is believed to be highly appropriate. A conceptual diagram of PET and a conceptual diagram wherein fluorescein was divided into the two moieties are shown in FIG. 3.

A fluorescent probe is a molecule being no fluorescent when a measuring object is not present, and having a function to emit fluorescence only when the probe traps a measuring object. Therefore, an ideal fluorescent probe can be obtained by designing a fluorescent probe whose fluorescence is quenched through PET under the former condition, and causes no PET under the latter condition. For example, it is readily possible to reveal by the experiment shown in Example 2 which level of oxidation potential is sufficient to lower the fluorescence, and easily be predicted, even for a new fluorophore, by measuring its reduction potential. The benzene ring moiety which acts as a PET donor moiety may be chosen so that its oxidation potential changes by a specific formation of a coordination bond or a reaction with a measuring object. Oxidation potentials of the PET donor moiety before and after the trapping are predictable by a quantum chemistry calculation. According to the steps above, the desired fluorescent probe can be designed without any synthetic process.

For example, when a fluorescent probe for measuring nitrogen monoxide is designed, a reaction rate of two adjacent amino groups present on the benzene ring (either amino group may have a substituent such as an alkyl group) with nitrogen monoxide is a factor that directly regulates measurement sensitivity. Therefore, electron density of the amino group is desired to be heightened by increasing electron density of the benzene ring moiety (i.e., it is desired to increase HOMO energy of the benzene ring moiety) to achieve high sensitivity. In conventionally used fluorescein, a carboxyl group as an electron withdrawing group is present, thereby the electron density of the benzene ring is lowered, and as a result, there arises a problem that the reactivity of the amino group decreases and thus the measurement sensitivity can not be heightened. In contrast, the compound of the present invention can be introduced with an electron donating group as a substituent of $R^3$, thereby the electron density of the benzene moiety can be increased so as to heighten the electron density of the amino group. Therefore, a fluorescent probe having excellent measurement sensitivity can be designed. Among such fluorescent probes, a fluorescent probe may be chosen whose fluorescence is quenched through PET when a measuring object is not present and causes no PET when the probe traps a measuring object to obtain a fluorescent probe having excellent measurement sensitivity and an ideal fluorescence property.

Example 5

Preparation of a Crown-ether-bound Fluorescein Derivative

Xanthone was prepared according to a method described in Proc. Indian. Acad. Sci. Sect. A., 57, 280(1963), and the resuling xanthone was converted to di(tert-butyldimethylsilyl) protected form (xanthone-TBDMS) (J. Biol. Chem., 264, 14, 8171(1989)).

4-Methyl catechol (3.5 g, 28 mmol) was dissolved in 100 ml of dichloromethane. The solution was stirred in a salt-ice bath at −1° C. to 0° C. and slowly added dropwise with a dichloromethane solution (20 ml) of bromine (5 g, 31 mmol). The dropping was terminated at the time point when white solid deposited, and the reaction solution was washed with a saturated aqueous ascorbic acid solution, and a saturated aqueous sodium chloride solution (100 ml each). The solvent was evaporated under reduced pressure to obtain white solid (4.1 g, yield 71%).

4-Bromo-5-methylcatechol (1.0 g, 4.9 mmol), tetraethylene glycol di-p-tosylate (2.5 g, 5.0 mmol), cesium fluoride (5 g, 33 mmol), and acetonitrile (100 ml) were put into a pear shape flask equipped with Dimroth condenser, and the mixture was refluxed under heating under argon atmosphere at 90° C. for 20 hours. The reaction solution was evaporated under reduced pressure. The residue was dissolved in a sufficient amount of ethyl acetate and the solution was filtrated to remove solids. The resulting filtrate was evaporated under reduced pressure to obtain 1.9 g of 4-bromo-5-methylbenzo-15-crown-5-ether as white solid. The solid was purified by NH silica gel column chromatography (eluent; ethyl acetate/methanol=20/1 (v/v)) to obtain white solid (0.69 g, yield 34%).

4-Bromo-5-methylbenzo-15-crown-5-ether (150 mg, 0.415 mmol) dissolved in 2-methyltetrahydrofuran (15 ml) was put in a two-neck flask dried well under argon atmosphere, and stirred in a liquid nitrogen/isopentane bath at about −150° C. To the solution, a t-butyl lithium/n-pentane solution (1.54 M, 1 ml) (1.54 mmol) was slowly added dropwise. After stirring for 30 minutes, the solution was slowly added dropwise with xanthone-TBDMS (190 mg, 0.416 mmol) dissolved in 3 ml of 2-methyltetrahydrofuran. After stirring for one hour, 2N aqueous hydrochloric acid was added, and the mixture was heated at 80° C. for one hour. The reaction solution was evaporated under reduced pressure, and the residue was dissolved in dichloromethane and washed with 2N aqueous hydrochloric acid. The organic layer was dried with anhydrous sodium sulfate, and the solvent was evaporated under reduced pressure to obtain red-orange crude oil product. The product was purified by alumina column chromatography (eluent; dichloromethane/methanol=15/1 (v/v)) to obtain the compound represented by the structure below as red-orange oil.

$^1$H-NMR(CDCl$_3$, 300 MHz)
Δ = 1.95 ppm (s, 3H, a)
3.8-4.2 (m, 16H, b)
6.66 (s, 1H, c)
6.86 (s, 1H, d)
6.91 (dd, 2H, e, Jef = 1.92)
7.05 (d, 2H, f)
7.31 (d, 2H, g, Jeg = 9.24)
MS(FAB) 492(MH$^+$)

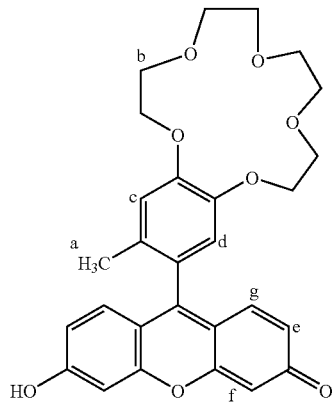

Example 6

The fluorescence quantum yield of the compound obtained in the above Example 5 was measured. The measurement was conducted by using F-4500 (HITACHI Ltd.). Fluorescence spectrum of the compound of Example 5 was analyzed in an aqueous solution of pH 9 containing NaCl or CaCl$_2$ using dimethylformamide (0.03%) as co-solvent. The pH of the solution for measurement was adjusted with addition of hydrochloric acid. The results are shown in the table below.

TABLE 1

| Concentration | Ca$^{2+}$ | Na$^+$ |
| --- | --- | --- |
| 3 M | 0.295 | 0.043 |
| 0.1 M | 0.02 | 0.03 |

Figure 4:
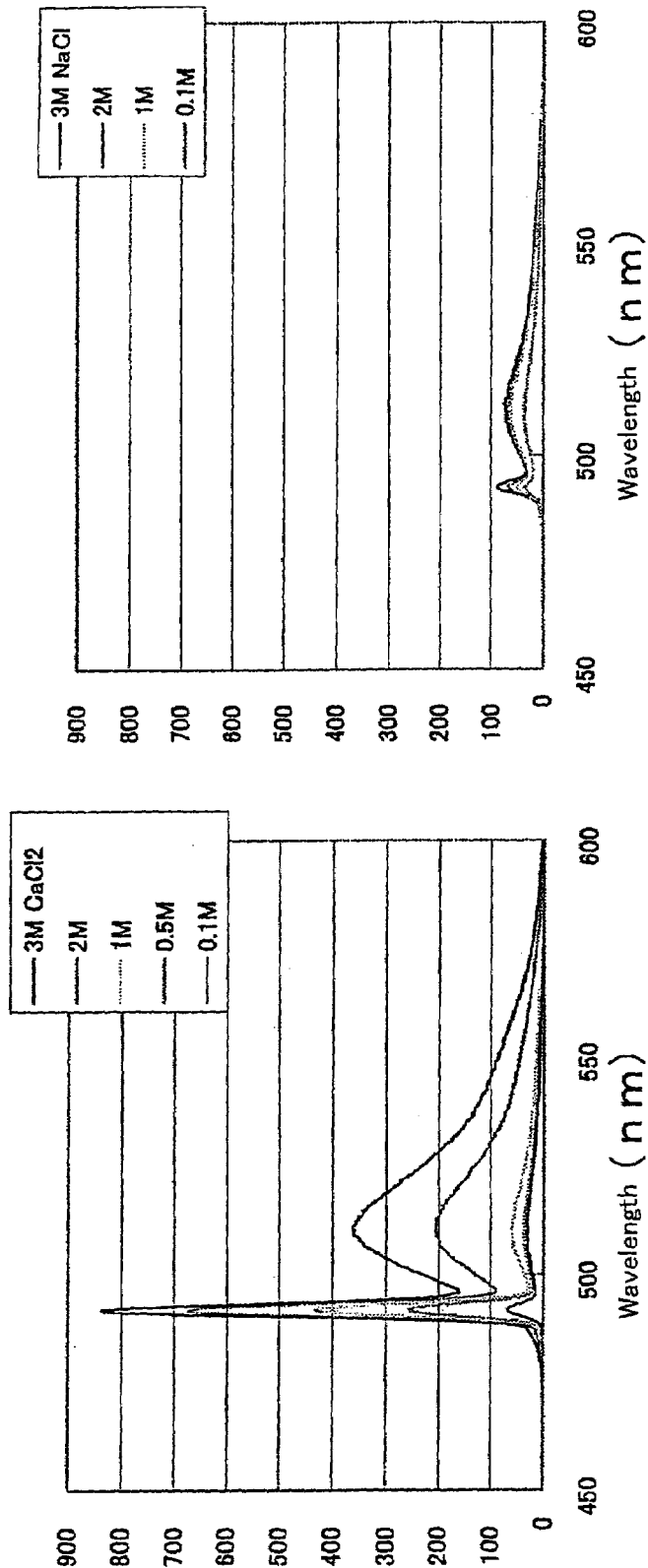
FIG. 4 shows changes of fluorescence spectra of the compound obtained in Example 5, which are dependent on concentration of NaCl or $CaCl_2$.

A dimethylformamide solution of the compound of Example 5 (the final concentration of 0.5 μM) was diluted with an aqueous solution of pH 9 containing NaCl or CaCl$_2$ and changes of fluorescence spectra depending on the NaCl or CaCl$_2$ concentrations were studied. The result is shown in FIG. 4.

Example 7

Preparation of a Crown-ether-bound Dichlorofluorescein Derivative 2,7-Dichloroxanthone was prepared according to a method described in J. Chem. Sci. (Lond), 3982(1955), Proc. Indian. Acad. Sci. Sect. A., 57, 280(1963), and J. Biol. Chem., 264, 14, 8171(1989). The obtained 2,7-dichloroxanthone was converted to di(tert-butyldimethylsilyl) protected form (2,7-dichloroxanthone-TBDMS).

4-Bromo-5-methylbenzo-15-crown-5-ether (150 mg, 0.415 mmol) dissolved in 2-methyltetrahydrofuran (15 ml) was put in a two-neck flask dried well under argon atmosphere, and stirred in a liquid nitrogen/isopentane bath at about −150° C. To the solution, a t-butyl lithium/n-pentane solution (1.54 M, 1 ml) (1.54 mmol) was slowly added dropwise. After stirring for 30 minutes, the solution was slowly added dropwise with 2,7-dichloroxanthone-TBDMS (190 mg, 0.416 mmol) dissolved in 3 ml of 2-methyltetrahydrofuran. After stirring for one hour, 2N aqueous hydrochloric acid was added, and the mixture was heated at 80° C. for one hour.

The reaction solution was evaporated under reduced pressure, and the residue was dissolved in dichloromethane and washed with 2N aqueous hydrochloric acid. The organic layer was dried with anhydrous sodium sulfate, and the solvent was evaporated under reduced pressure to obtain red-orange crude oil product. The product was purified by silica gel column chromatography (eluent; dichloromethane/methanol=7/1 (v/v)) to obtain the compound represented by the structure below as red-orange oil.

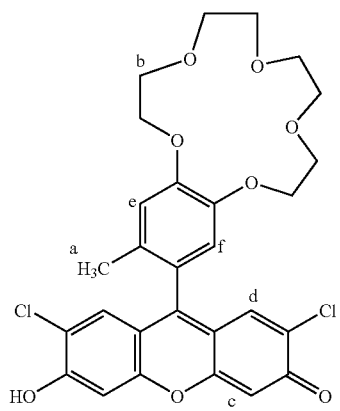

$^1$H-NMR(CDCl$_3$, 300 MHz)
Δ = 1.94 ppm (s, 3H, a)
3.6-4.2 (m, 16H, b)
6.26 (s, 2H, c)
6.81 (s, 2H, d)
6.84 (s, 1H, e)
7.04 (s, 1H, f)
MS(FAB) 583 (MNa$^+$)
585(M + 2Na$^+$)

Example 8

Figure 5:
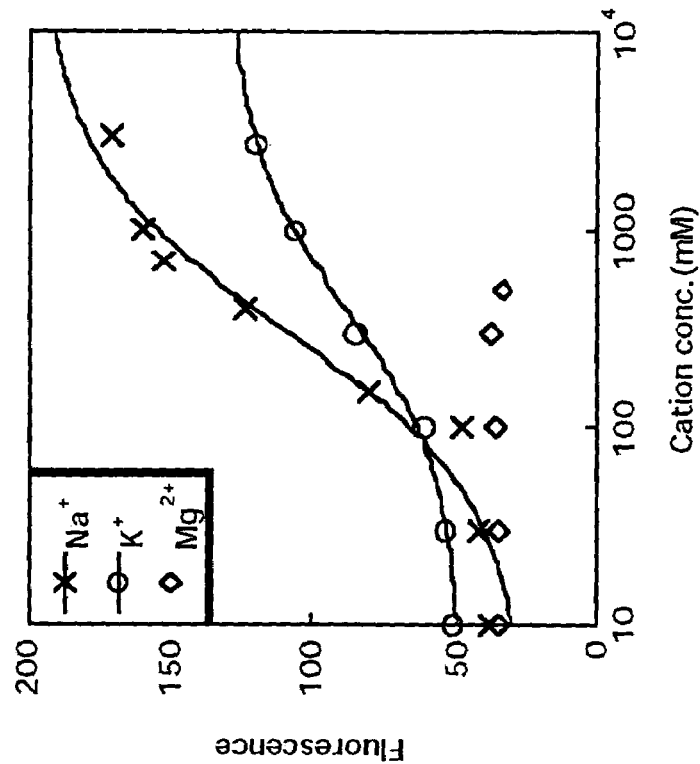
FIG. 5 shows changes of fluorescence of the compounds obtained in Example 5 (left) and Example 7 (right) caused by additions of various cations.
Figure 5:
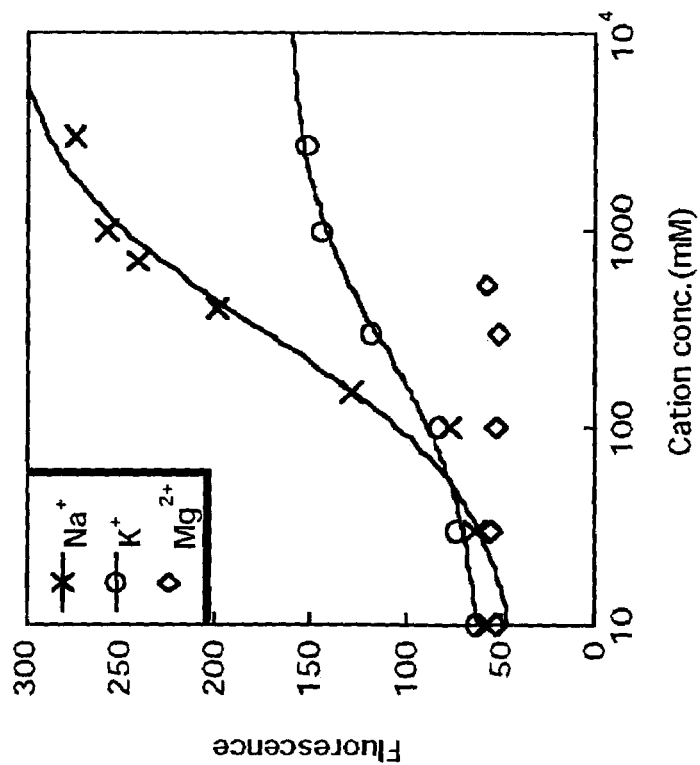

Fluorescence intensity changes of the compound obtained in Example 5 and the compound obtained in Example 7 above were measured with addition of sodium, magnesium, and potassium. Measurements were conducted in 0.2 M Tris-perchlorate buffers at pH 7.5 containing various concentrations of sodium perchlorate and magnesium perchlorate using dimethylformamide (0.1%) as co-solvent when sodium and magnesium were added, and in 0.2 M Tris-hydrochloride buffers at pH 7.5 containing various concentrations of potassium chloride using dimethylformamide (0.1%) as co-solvent when potassium was added. The final concentrations of the compounds obtained in Example 5 and Example 7 were adjusted to be 3 μM. The compound obtained in Example 5 was measured at excitation wavelength of 492 nm and fluorescence wavelength of 513 nm and the compound obtained in Example 7 was measured at excitation wavelength of 504 nm and fluorescence wavelength of 524 nm. The results of measurements are shown in FIG. 5. The results of calculations of complex formation constants from the above results are shown below.

TABLE 2

| | Complex formation constant (mM) | | |
| --- | --- | --- | --- |
| | Na$^+$ | K$^+$ | Mg$^+$ |
| Compound of Example 5 | 0.31 | 0.25 | Unmeasurable |
| Compound of Example 7 | 0.32 | 0.41 | Unmeasurable |

Example 9

Figure 6:
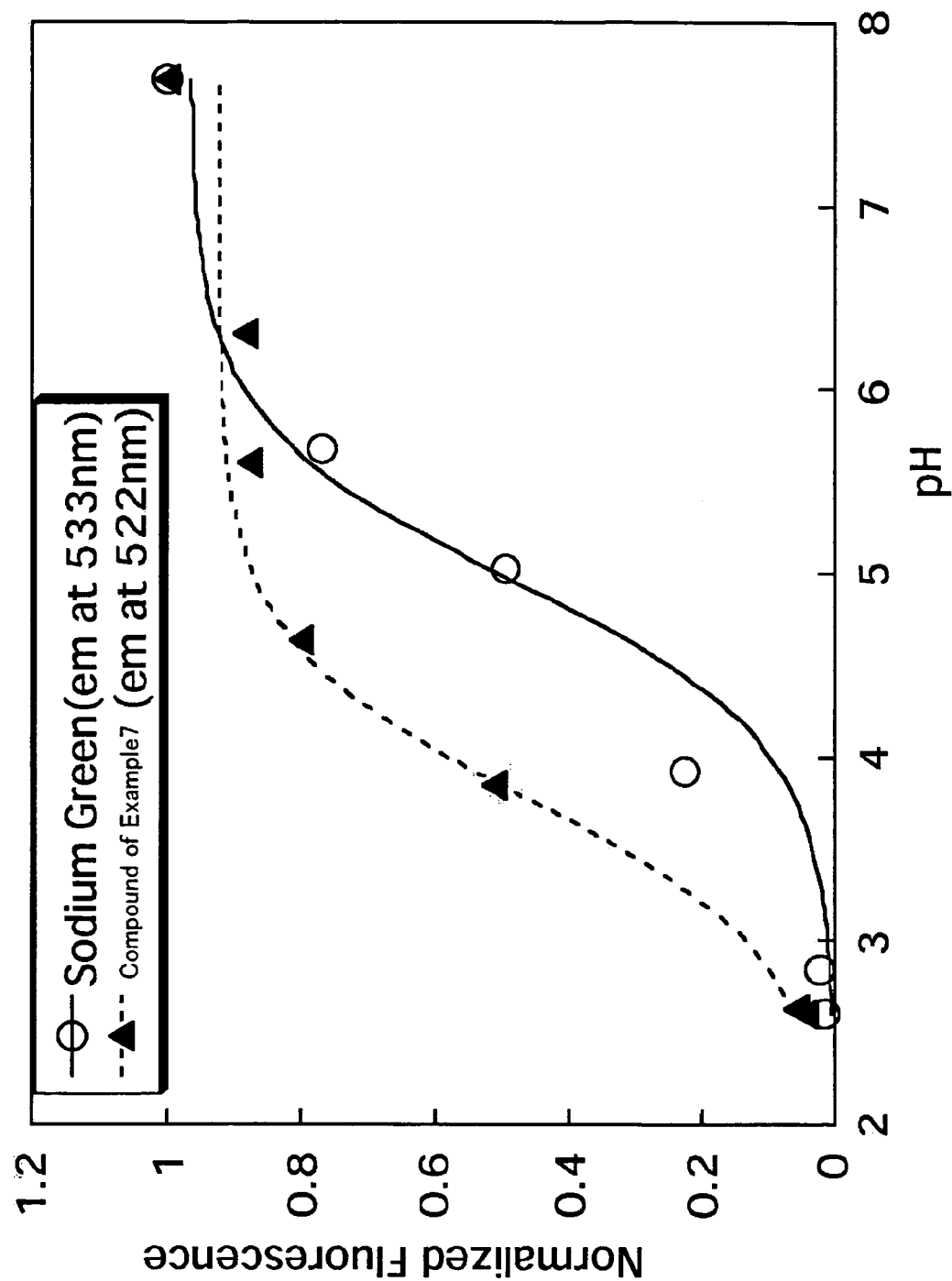
FIG. 6 shows changes of fluorescence intensities versus pH change of the compound obtained in Example 7 and Sodium Green, tetra(tetramethylammonium) salt.

Fluorescence intensity changes of the compound obtained in Example 7 and Sodium Green tetra(tetramethylammonium)salt (Molecular Probes Inc.) against pH change were studied under co-presence of sodium. Measurements were conducted in 0.2 M Tris-phosphate buffers at various pH containing 500 mM of sodium perchlorate using dimethylformamide (0.1%) as a co-solvent. The compound obtained in Example 7 was measured at excitation wavelength of 504 nm and fluorescence wavelength of 522 nm and Sodium Green tetra(tetramethylammonium)salt was measured at excitation wavelength of 508 nm and fluorescence wavelength of 533 nm. The measurement results are shown in FIG. 6.

The compound obtained in Example 7 had a stable fluorescence intensity up to around pH5, and thus found to be a probe which is less susceptible to a pH change compared with Sodium Green tetra(tetramethylammonium)salt.

INDUSTRIAL APPLICABILITY

According to the present invention, a fluorescent probe having an excellent fluorescent property is provided. Further, according to the design method of the present invention, a fluorescent probe having an excellent fluorescent property can be logically designed.

What is claimed is:
1. A fluorescent probe which is represented by the following formula (I):

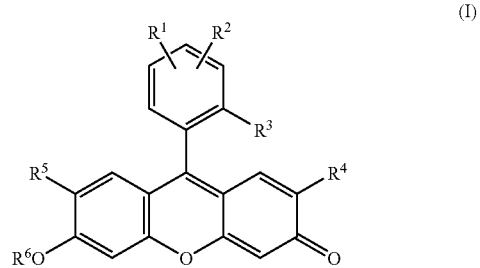

wherein,
R$^1$ and R$^2$ each independently represents hydrogen atom, or a substituent for trapping proton, a metal ion, or an active oxygen species, provided that both of R$^1$ and R$^2$ do not simultaneously represent hydrogen atoms, or R$^1$ and R$^2$ may combine to each other to form a ring structure for trapping proton, a metal ion, or active oxygen species;
R$^3$ is a lower alkyl group or a lower alkoxy group;
R$^4$ and R$^5$ each independently represents hydrogen atom or a halogen atom;
R$^6$ represents hydrogen atom, an alkylcarbonyl group, or an alkylcarbonyloxymethyl group, provided that a combination of R$^1$, R$^2$, and R$^3$ provides:
 (1) substantially high electron density of the benzene ring to which said groups bind so that the compound represented by the formula (I) is substantially no fluorescent before the trapping of proton, a metal ion, or an active oxygen species, and
 (2) substantially reduced electron density of the benzene ring to which said groups bind so that a compound after the trapping, which is derived from the compound represented by the formula (I), is substantially highly fluorescent after the trapping of proton, a metal ion, or an active oxygen species.

2. The fluorescent probe according to claim 1, wherein the oxidation potential of said benzene ring before the trapping of proton, a metal ion, or an active oxygen species is less than 1.40 V, and oxidation potential of said benzene ring after trapping of proton, a metal ion, or an active oxygen species is 1.40 V or higher, and said oxidation potential of said benzene ring increases by 0.20 V or higher after the trapping, under a sufficiently basic condition so that the hydroxy group of the xanthene ring can become a complete anion when $R^6$ is hydrogen atom.

3. The fluorescent probe according to claim 1, wherein the oxidation potential of said benzene ring before the trapping of proton, a metal ion, or an active oxygen species is less than 1.70 V, and the oxidation potential of said benzene ring after the trapping of proton, a metal ion, or an active oxygen species is 1.70 V or higher, and the oxidation potential of said benzene ring increases by 0.20 V or higher after the trapping, under a sufficiently acidic condition so that the hydroxy group of the xanthene ring can exist in a non-dissociation state when $R^6$ is hydrogen atom.

4. The fluorescent probe according to claim 1, wherein the metal ion is an alkali metal ion, calcium ion, magnesium ion, or zinc ion.

5. The fluorescent probe according to claim 1, wherein the active oxygen species is selected from the group consisting of nitrogen monoxide, hydroxy radical, singlet oxygen, and superoxide.

6. The fluorescent probe according to claim 1, which is for measuring zinc ion or nitrogen monoxide and wherein either or both of $R^1$ and $R^2$ are a group represented by the following formula (A):

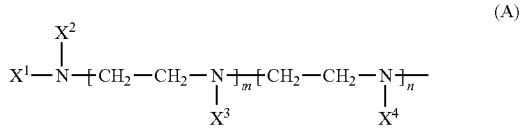

wherein $X^1$, $X^2$, $X^3$, and $X^4$ each independently represents hydrogen atom, an alkyl group, 2-pyridylmethyl group, or a protective group of amino group, and m and n each independently represents 0 or 1.

7. The fluorescent probe according to claim 1, which is for measuring singlet oxygen and wherein $R^1$ and $R^2$ combine to each other to represent a ring structure represented by the following formula (B):

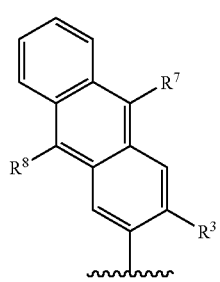

wherein $R^7$ and $R^8$ each independently represents a $C_{1-4}$ alkyl group or an aryl group.

8. A method for designing a fluorescent probe which is represented by the following formula (I) following formula (I):

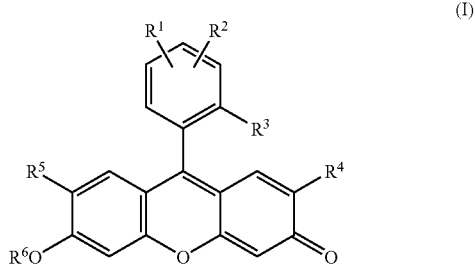

wherein,
$R^1$ and $R^2$ each independently represents hydrogen atom, or a substituent for trapping proton, a metal ion, or an active oxygen species, provided that both of $R^1$ and $R^2$ do not simultaneously represent hydrogen atoms, or $R^1$ and $R^2$ may combine to each other to form a ring structure for trapping proton, a metal ion, or an active oxygen species;

$R^3$ is a lower alkyl group or a lower alkoxy group;

$R^4$ and $R^5$ each independently represents hydrogen atom or a halogen atom; $R^6$ represents hydrogen atom, an alkylcarbonyl group, or an alkylcarbonyloxymethyl group), which comprises selecting, as a combination of $R^1$, $R^2$, and $R^3$, the combination which provides:

(1) substantially high electron density of the benzene ring to which said groups bind so that the compound represented by the formula (I) is substantially no fluorescent before the trapping of proton, a metal ion, or an active oxygen species, and (2) substantial reduced electron density of the benzene ring to which said groups bind so that a compound after the trapping, which is derived from the compound represented by the formula (I), is substantially highly fluorescent after the trapping of proton, a metal ion, or an active oxygen species.

9. A fluorescent probe obtained from the method according to claim 8.

10. The fluorescent probe according to claim 2, wherein the metal ion is an alkali metal ion, calcium ion, magnesium ion, or zinc ion.

11. The fluorescent probe according to claim 3, wherein the metal ion is an alkali metal ion, calcium ion, magnesium ion, or zinc ion.

12. The fluorescent probe according to claim 2, wherein the active oxygen species is selected from the group consisting of nitrogen monoxide, hydroxy radical, singlet oxygen, and superoxide.

13. The fluorescent probe according to claim 3, wherein the active oxygen species is selected from the group consisting of nitrogen monoxide, hydroxy radical, singlet oxygen, and superoxide.

14. The fluorescent probe according to claim 2, which is for measuring zinc ion or nitrogen monoxide and wherein either or both of $R^1$ and $R^2$ are a group represented by the following formula (A):

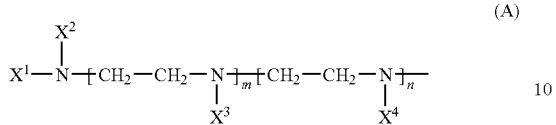
(A)

wherein $X^1$, $X^2$, $X^3$, and $X^4$ each independently represents hydrogen atom, an alkyl group, 2-pyridylmethyl group, or a protective group of amino group, and m and n each independently represents 0 or 1.

15. The fluorescent probe according to claim 3, which is for measuring zinc ion or nitrogen monoxide and wherein either or both of $R^1$ and $R^2$ are a group represented by the following formula (A):

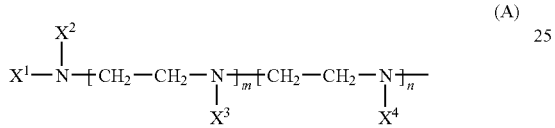
(A)

wherein $X^1$, $X^2$, $X^3$, and $X^4$ each independently represents hydrogen atom, an alkyl group, 2-pyridylmethyl group, or a protective group of amino group, and m and n each independently represents 0 or 1.

16. The fluorescent probe according to claim 2, which is for measuring singlet oxygen and wherein $R^1$ and $R^2$ combine to each other to represent a ring structure represented by the following formula (B):

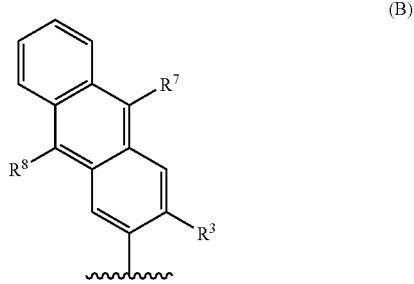
(B)

wherein $R^7$ and $R^8$ each independently represents a $C_{1-4}$ alkyl group or an aryl group.

17. The fluorescent probe according to claim 3, which is for measuring singlet oxygen and wherein $R^1$ and $R^2$ combine to each other to represent a ring structure represented by the following formula (B):

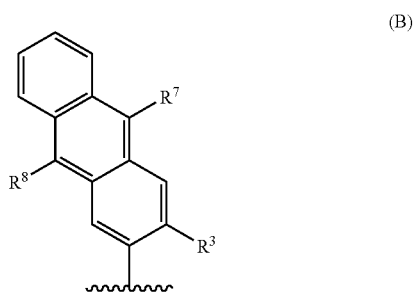
(B)

wherein $R^7$ and $R^8$ each independently represents a $C_{1-4}$ alkyl group or an aryl group.

* * * * *

UNITED STATES PATENT AND TRADEMARK OFFICE
CERTIFICATE OF CORRECTION

PATENT NO. : 7,524,974 B2  
APPLICATION NO. : 10/519682  
DATED : April 28, 2009  
INVENTOR(S) : Nagano et al.

Page 1 of 1

It is certified that error appears in the above-identified patent and that said Letters Patent is hereby corrected as shown below:

On Cover Page, of the printed patent, paragraph [73] Assignees, the Assignees "Tetsuo Nagano, Tokyo (JP); Daiichi Pure Chemicals Co., Ltd., Tokyo (JP)" should be --Tetsuo Nagano, Tokyo (JP); Sekisui Medical Co., Ltd., Tokyo (JP)--.

Signed and Sealed this

Thirteenth Day of October, 2009

David J. Kappos  
*Director of the United States Patent and Trademark Office*